US008546382B2

(12) United States Patent
Naveiras et al.

(10) Patent No.: US 8,546,382 B2
(45) Date of Patent: Oct. 1, 2013

(54) METHODS FOR ENHANCING HEMATOPOIETIC PROGENITOR CELL ENGRAFTMENT

(75) Inventors: Olaia Naveiras, Lausanne (CH); George Daley, Weston, MA (US); Pamela L. Wenzel, Chestnut Hill, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/264,423

(22) PCT Filed: Apr. 15, 2010

(86) PCT No.: PCT/US2010/031209
§ 371 (c)(1),
(2), (4) Date: Dec. 28, 2011

(87) PCT Pub. No.: WO2010/121008
PCT Pub. Date: Oct. 21, 2010

(65) Prior Publication Data
US 2012/0101067 A1    Apr. 26, 2012

Related U.S. Application Data

(60) Provisional application No. 61/169,416, filed on Apr. 15, 2009.

(51) Int. Cl.
*A61K 31/535* (2006.01)
*A61K 31/425* (2006.01)
*A01N 43/24* (2006.01)

(52) U.S. Cl.
USPC ........ 514/228.8; 514/107; 514/219; 514/342; 514/357; 514/365; 514/369; 514/411; 514/418; 514/475; 514/567; 514/568; 514/629

(58) Field of Classification Search
USPC .............. 514/107, 219, 228.8, 342, 357, 365, 514/369, 411, 418, 475, 567, 568, 629
See application file for complete search history.

(56) References Cited

U.S. PATENT DOCUMENTS 7,169,750 B2 * 1/2007 Bridger et al. ............... 424/85.1
7,442,390 B2   10/2008 Seshi

OTHER PUBLICATIONS

Maitra, B., et al., "Human mesenchymal stem cells support unrelated donor hematopoietic stem cells and suppress T-cell activation." Bone Marrow Transplantation, 2004, vol. 33, pp. 597-604.
Gimble, J.M. et al, "The function of adipocytes in the bone marrow stroma: an update." Bone, 1996, vol. 19, No. 5, pp. 421-428.
Laharrague, P. et al., "High expression of leptin by human bone marrow adipocytes in primary culture." The FASEB Journal, 1998, vol. 12, pp. 747-752.
Naveiras, O. et al., "Bone-marrow adipocytes as negative regulators of the haematopoietic microenvironment." Nature, Jul. 2009, vol. 460, No. 9. pp. 259-264.
Belaid-Choucair et al,, Human bone marrow adipocytes block granulopoiesis through neuropilin-1-induced granulocyte colony-stimulating factor inhibition. Stem Cells. Jun. 2008;26(6):1556-64. doi: 10.1634/stemcells.2008-0068. Epub Apr. 3, 2008.
Bujalska et al., A novel selective 11beta-hydroxysteroid dehydrogenase type 1 inhibitor prevents human adipogenesis. J Endocrinol. May 2008;197(2):297-307. doi: 10.1677/JOE-08-0050.
Calvi et al., Osteoblastic cells regulate the haematopoietic stem cell niche. Nature. Oct. 23, 2003;425(6960):841-6.
Calvo et al., Regeneration of blood-forming organs after autologous leukocyte transfusion in lethally irradiated dogs. II. Distribution and cellularity of the marrow in irradiated and transfused animals. Blood. Apr. 1976;47(4):593-601.
Christensen et al., Flk-2 is a marker in hematopoietic stem cell differentiation: a simple method to isolate long-term stem cells. Proc Natl Acad Sci U S A. Dec. 4, 2001;98(25):14541-6. Epub Nov. 27, 2001.
Dimascio et al., Identification of adiponectin as a novel hemopoietic stem cell growth factor. J Immunol. Mar. 15, 2007;178(6):3511-20.
Kiel et al., SLAM family receptors distinguish hematopoietic stem and progenitor cells and reveal endothelial niches for stem cells. Cell. Jul. 1, 2005;121(7):1109-21.
Lazarenko et al., Rosiglitazone induces decreases in bone mass and strength that are reminiscent of aged bone. Endocrinology. Jun. 2007;148(6):2669-80. Epub Mar. 1, 2007.
Maaravi et al., Mild, reversible pancytopenia induced by rosiglitazone. Diabetes Care. Jun. 2005:28(6):1536.
Moitra et al., Life without white fat: a transgenic mouse. Genes Dev. Oct. 15, 1998;12(20):3168-81.
Nishikawa et al., Changes in hematopoiesis-supporting ability of C3H10T1/2 mouse embryo fibroblasts during differentiation. Blood. Mar. 1, 1993;81(5):1184-92.
Tavassoli et al., Induction of sustained hemopoiesis in fatty marrow. Blood. Jan. 1974;43(1):33-8.
Wright et al., A synthetic antagonist for the peroxisome proliferator-activated receptor gamma inhibits adipocyte differentiation. J Biol Chem. Jan. 21, 2000;275(3):1873-7.
Yan et al., The adipokine lipocalin 2 is regulated by obesity and promotes insulin resistance. Diabetes. Oct. 2007;56(10):2533-40. Epub Jul. 16, 2007.
Yang et al., Identification of Lin(−)Scal(+)kit(+)CD34(+)Flt3- short-term hematopoietic stem cells capable of rapidly reconstituting and rescuing myeloablated transplant recipients. Blood. Apr. 1, 2005;105(7):2717-23. Epub Nov. 30, 2004.
Yokota et al., Adiponectin, a new member of the family of soluble defense collagens, negatively regulates the growth of myelomonocytic progenitors and the functions of macrophages. Blood. Sep. 1, 2000;96(5):1723-32.
Zhang et al., Identification of the haematopoietic stem cell niche and control of the niche size. Nature. Oct. 23, 2003;425(6960):836-41.
Zhang et al., Tumor necrosis factor (TNF) is a physiologic regulator of hematopoietic progenitor cells: increase of early hematopoietic progenitor cells in TNF receptor p55-deficient mice in vivo and potent inhibition of progenitor cell proliferation by TNF alpha in vitro. Blood. Oct. 15, 1995;86(8):2930-7.

* cited by examiner

*Primary Examiner* — My-Chau T Tran
(74) *Attorney, Agent, or Firm* — Wolf, Greenfield & Sacks, P.C.

(57) ABSTRACT

Described herein are methods for improving engraftment of hematopoietic cells in an individual following hematopoietic progenitor cell transplantation (e.g., via bone marrow or cord blood transplantation). Methods for increasing hematopoietic progenitor cell proliferation in individuals with bone marrow aplasia are also described. The methods involve administering an agent that inhibits adipogenesis, adipocyte growth, adipocyte differentiation and/or adipocyte proliferation.

18 Claims, 27 Drawing Sheets

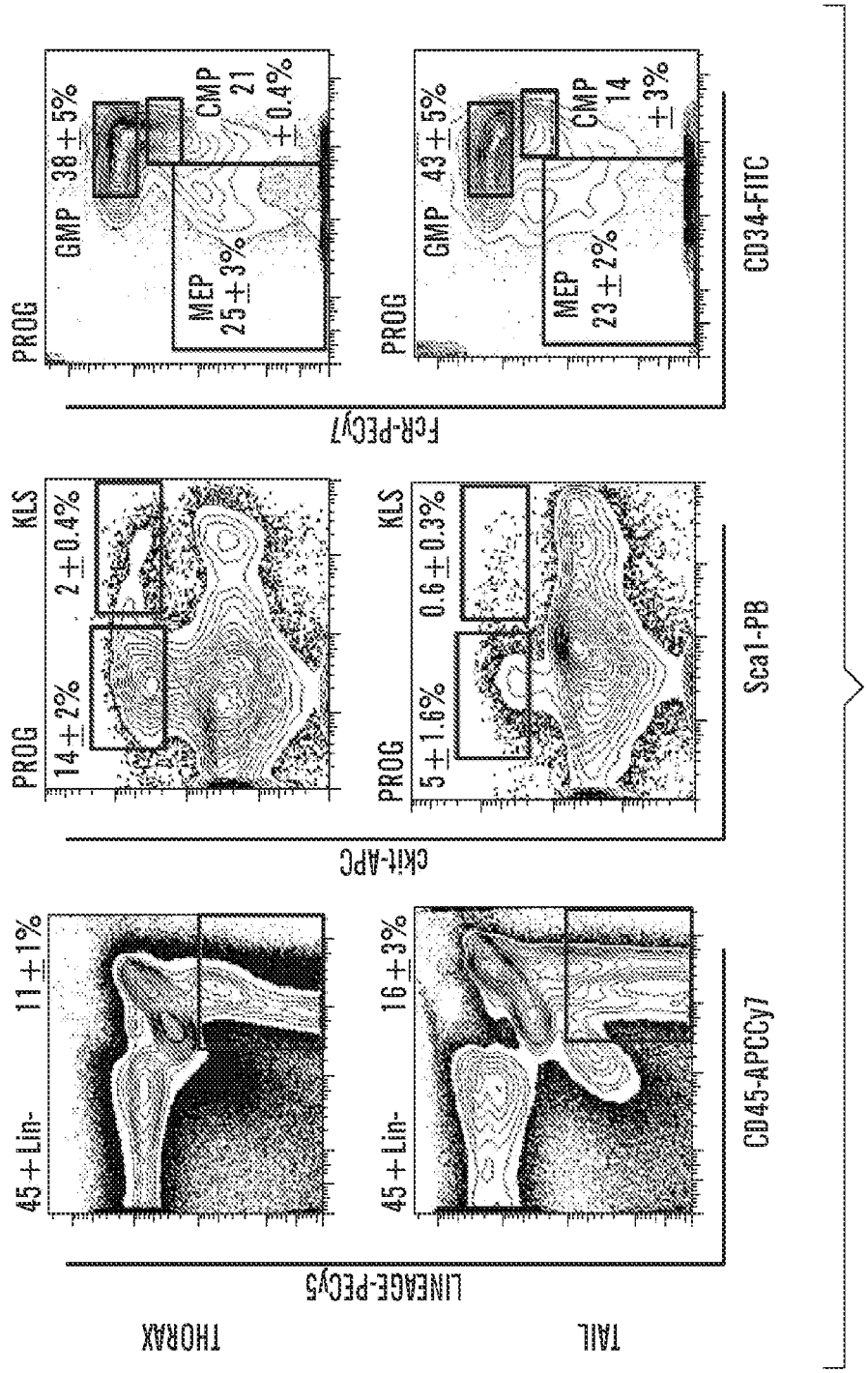

METHODS FOR ENHANCING HEMATOPOIETIC PROGENITOR CELL ENGRAFTMENT

CROSS REFERENCE TO RELATED APPLICATIONS

This application is a 35 U.S.C. §371 National Phase Entry Application of International Application No. PCT/US2010/031209 filed Apr. 15, 2010, which designates the United States, and which claims benefit under 35 U.S.C. §119(e) of U.S. Provisional Application No. 61/169,416 filed Apr. 15, 2009, the contents of all of which are incorporated herein by reference in their entirety entireties.

FIELD OF THE INVENTION

The present invention relates to methods for enhancing engraftment of hematopoietic progenitor cells. Methods for increasing hematopoietic progenitor cell expansion in an individual are also provided.

BACKGROUND

Hematopoietic stem and progenitor cell transplantation is used in the treatment of a wide variety of hematologic disorders, malignancies, and genetic diseases of the blood and blood forming cells. For example, hematopoietic progenitor cell transplantation is currently used to treat bone marrow destruction caused by irradiation and/or alkylating therapy in the treatment of cancer. Transplantation of hematopoietic stem and progenitor cells (e.g., short term progenitor cells) can be either "allogeneic" (cells are from another donor) or "autologous" (cells originate from the same individual). Hematopoietic progenitor cells useful for transplantation can be derived from bone marrow, peripheral blood, or umbilical cord blood.

Hematopoietic progenitor cells are responsible for hematopoietic recovery during the early post-transplant period. However, in some cases progenitor cell engraftment fails to occur due to e.g., micro-environmental defects as part of the underlying disease (e.g., aplastic anemia), stromal cell damage caused by chemoradiotherapy and development of graft-versus-host disease. In addition, while hematopoietic progenitor cells derived from cord blood may be preferred due to the low incidence of graft versus host disease, cord blood transplantations also have a slow rate of progenitor cell engraftment and hematopoietic recovery.

Thus, there is a need for the development of methods that improve engraftment of hematopoietic progenitor cells.

SUMMARY OF THE INVENTION

Described herein are methods for enhancing engraftment of hematopoietic progenitor cells following transplantation. Methods for increasing hematopoietic progenitor cell proliferation in an individual are also described. Embodiments of the invention are based, in part, on the observation that hematopoiesis is reduced in adipocyte rich marrow during homeostasis and that adipocytes antagonize marrow recovery post-irradiation.

In one embodiment the methods involve administering an agent that alters adipocyte metabolism to an individual following bone marrow transplantation, which enhances engraftment and/or increases hematopoietic progenitor cell proliferation.

In one aspect, a method is described herein for enhancing hematopoietic stem cell engraftment in an individual following hematopoietic progenitor cell transplantation, the method comprising administering to the individual an agent that alters adipocyte metabolism, thereby enhancing hematopoietic progenitor cell engraftment.

In one embodiment of this aspect and all other aspects described herein, the hematopoietic progenitor cells are derived from or are present in bone marrow. In another embodiment of this aspect and all other aspects described herein, the hematopoietic progenitor cells are derived from or are present in cord blood. In another embodiment, the hematopoietic progenitor cells are derived from or present in peripheral blood.

In one embodiment of this aspect and all other aspects described herein, the agent is selected from the group consisting of a PPAR gamma inhibitor, an ap2/FABP4 inhibitor, and an 11 beta-hydrosteroid dehydrogenase inhibitor.

In another embodiment of this aspect and all other aspects described herein, the PPAR gamma inhibitor is selected from the group consisting of bispheno-A-diglycidyl-ether (BADGE), 2-chloro-5-nitro-N-4-pyridinyl-benzamide (T0070907), 2-chloro-5-nitrobenzanilide (GW9662), (4-chlorophenyl)-(diemethoxyphosphinyl)-methyl-phosphoric acid-dimethyl ester (mifobate; SR-202), 2-((5,5,8,8-tetramethyl-5,6,7,8-tetrahydro-2-naphthyl)carbonyl)benzoic acid (LG 100641), propanamide, 2,2-dimethyl-N-[5-nitro-3-(2-propen-1-yl)-2(3H)-thiazolylidene] (PD068235); diclofenac; MK886; (2-thiophenecarboxylic acid, 3-[[[2-methoxy-4-(phenylamino)phenyl]amino]sulfonyl]-methyl ester (GSK0660); benzoic acid, 2-[(5,6,7,8-tetrahydro-5,5,8,8-tetramethyl-2-naphthalenyl)carbonyl]-) (LG100641); benzoic acid, 4-(7,8,9,10-tetrahydro-5,7,7,10,10-[entamethyl-2-nitro-5H-benzo[b]naphtho[2,3-e][1,4]diazepin-12-yl)-) (HX531); and ((4-2((2S,5S)-5-2(-(bis(phenylmethyl)amino)-2-oxoethyl)-2-heptyl-4-oxo-3-thiazolidinyl)butyl)-benzoic acid) (GW0072). In another embodiment of this aspect and all other aspects described herein, the ap2/FABP4 inhibitor is selected from the group consisting of BMS309403, N-benzyl-hexahydrocyclohepta[b]indole, and 1,3-oxazinan-2-one and derivatives thereof.

In another embodiment of this aspect and all other aspects described herein, the 11 beta-hydrosteroid dehydrogenase inhibitor is selected from the group consisting of PF877423, BVT.2733, 4-thiazoleacetamide, 2-[[(3-chloro-2-methylphenyl)sulfonyl]amino]-N,N-diethyl-2-[2-[[3-Chloro-2-methylphenyl_sulfonyl]amino]-1,3-thiazol-4-yl]-N,N-diethylacetamide (BVT.14225), and trifluoromethyl thiazolone.

In another aspect, the methods described herein relate to a method for increasing hematopoietic progenitor cell proliferation in an individual following hematopoietic progenitor cell transplantation, the method comprising administering to the individual an agent that alters adipocyte metabolism, wherein the agent increases hematopoietic progenitor cell proliferation.

Definitions

The term "engraftment" is used herein to refer to the ability of hematopoietic progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s)

into which stem cells have homed, colonized, or become engrafted; or by evaluation of the progress of a subject through disease progression, survival of hematopoietic progenitor cells, or survival of a recipient. In one embodiment, engraftment is determined by measuring white blood cell counts in peripheral blood during a post-transplant period. Alternatively, engraftment can be assessed by measuring recovery of marrow cells in a bone marrow aspirate sample.

As used herein, the term "enhancing hematopoietic progenitor cell engraftment" refers to an increase in the efficiency or rate (i.e., amount of engraftment over a period of time) of hematopoietic progenitor cell engraftment of at least 10% (e.g., as assessed by measuring white blood cell count) in individuals treated with an agent compared to untreated individuals. Preferably the rate of hematopoietic progenitor cell engraftment is increased by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 500-fold, at least 1000-fold or higher in individuals being treated with an agent compared to the efficiency/rate of engraftment in an untreated individual. Engraftment can also be assessed using a bone marrow aspirate sample and monitoring colony forming unit cells (CFU-Cs).

As used herein, the term "agent" refers to any chemical, small molecule, nucleic acid sequence, protein, peptide, aptamer, antibody, and functional fragments or derivatives thereof that can be used to alter adipocyte metabolism.

As used herein, the term "adipocyte" is used to encompass adipocytes, pre-adipocytes and adipocyte progenitor cells (e.g., mesenchymal stem cells). The term "adipocyte" can encompass cells from both white and/or brown adipose stores in an individual or animal.

As used herein, the term "alters adipocyte metabolism" refers to an effect of an agent on at least one metabolic pathway of an adipocyte, a pre-adipocyte or an adipocyte progenitor cell that results in a reduction of adipogenesis, a reduction in adipocyte growth, a reduction of proliferation, or a reduction of differentiation by at least 10% as assessed by an adipocyte proliferation assay. It is preferred that the reduction in adipogenesis, or reduction in adipocyte growth, or reduction in adipocyte proliferation or reduction in adipocyte differentiation is at least 20%, at least 30%, at least 40%, at least 50%, at least 60%, at least 70%, at least 80%, at least 90%, at least 95%, at least 99%, or even 100% (i.e., absent) in cells treated with an agent that alters adipocyte metabolism compared to untreated adipocyte cells. In some embodiments, the agent that "alters adipocyte metabolism" can also promote cell death of an adipocytic cell (i.e., greater than 100% reduction in proliferation or growth). In general, the effect of an agent on adipocyte metabolism can be determined using data from in vitro and/or animal studies. However, it is also contemplated herein that an agent can be assessed for an in vivo effect on adipocyte metabolism by monitoring adipocyte number in e.g., bone marrow aspirate of an individual following administration of a candidate agent.

As used herein, the term "hematopoietic progenitor cells" encompasses pluripotent cells capable of differentiating into several cell types of the hematopoietic system, including, but not limited to, granulocytes, monocytes, erythrocytes, megakaryocytes, B-cells and T-cells. Hematopoietic progenitor cells are committed to the hematopoietic cell lineage and generally do not self-renew; hematopoietic progenitor cells can be identified, for example by cell surface markers such as Lin-KLS+Flk2-CD34+. The term "hematopoietic progenitor cells" encompasses short term hematopoietic stem cells (ST-HSCs), multi-potent progenitor cells (MPPs), common myeloid progenitor cells (CMPs), granulocyte-monocyte progenitor cells (GMPs), and megakaryocyte-erythrocyte progenitor cells (MEPs). The term "hematopoietic progenitor cells" does not encompass hematopoietic stem cells capable of self-renewal, which can be identified with the following stem cell marker profile: Lin-KLS+Flk2-CD34-. The presence of hematopoietic progenitor cells can be determined functionally as colony forming unit cells (CFU-Cs) in complete methylcellulose assays, or phenotypically through the detection of cell surface markers using assays known to those of skill in the art.

As used herein, the term "increasing hematopoietic progenitor cell expansion" refers to an increase in hematopoietic progenitor cell proliferation following a hematopoietic progenitor cell transplant (e.g., bone marrow, peripheral blood, or cord blood transplant) of at least 10% (as assessed by for example, measuring hematopoietic progenitor number in a bone marrow aspirate sample) in the bone marrow of an individual being treated with an agent that alters adipocyte metabolism compared to an untreated individual. It is preferred that the increase in hematopoietic progenitor cell number is at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 50-fold, at least 100-fold, at least 500-fold, at least 1000-fold or higher in the presence of an agent that alters adipocyte metabolism than the level of hematopoietic progenitor cell proliferation in the absence of such agent.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

1a. Absolute number of hematopoietic cells (CD45+) per vertebral segment. 1b. Absolute frequency of progenitors within the hematopoietic compartment (CD45+) as determined by flow cytometry. 1c. Competitive transplantation (250,000 45.1 tail or thorax BM against 250,000 45.2 femoral BM), 1d. day 13 spleen colony assay, and 1e. colony forming unit (CFU) progenitor assay from tail and thorax BM. 1f. Cell cycle analysis (DAPI-DNA stain) per progenitor compartment. Bars indicate average % cells in S/G2/M transition±SEM. 1g. 100 tail and thorax BM sorted HSC (ckit+Lin-Sca1+Flk2–; >95% purity) were transplanted competitively, then analyzed at 5 weeks and 12 weeks post-transplant for engraftment in peripheral blood. 1h. CD34 expression within the HSC fraction (KLSF, ckit+Lin-Sca1+Flk2–); numbers indicate the percentage of CD34low within the KLSF fraction.

FIGS. 2a-f: The lack of bone marrow adipocytes post-irradiation in fatless mice enhances hematopoietic progenitor expansion and post-transplant recovery.

2a. Experimental design. Wildtype FVB or fatless FVB.A-ZIP/F1 6 week-old mice (CD45.1) were lethally irradiated and transplanted with 200,000 CD45.2, MHC-compatible DBA/1 wild-type BM. Femurs were isolated on day 17-20 post-transplant and the donor DBA CD45.2 wildtype BM was recovered by high purity FACS, then used for progenitor assays or competitive serial transplantation. 2b. White blood cell (WBC) counts and 2c. hemoglobin levels in peripheral blood after primary transplant. BM recovered from primary transplants was assayed for 2d. relative frequency of progenitors by FACS (±STD) 2e. colony forming units assay (CFU), and 2f. secondary competitive transplantation into wildtype recipients.

Figure 3A:
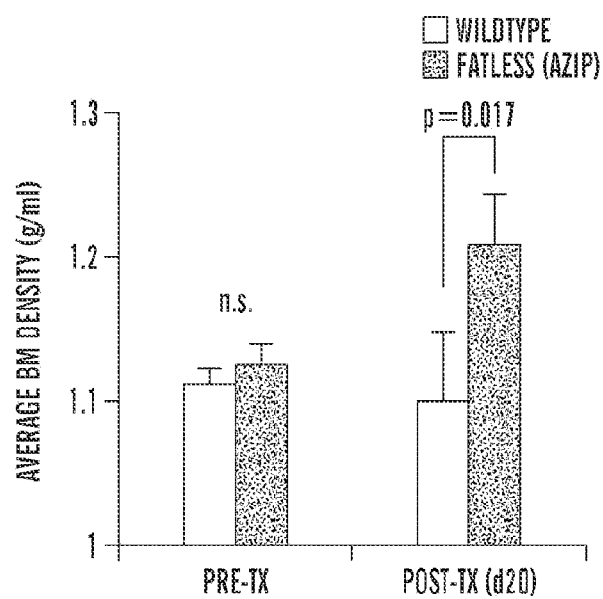
Figure 3B:
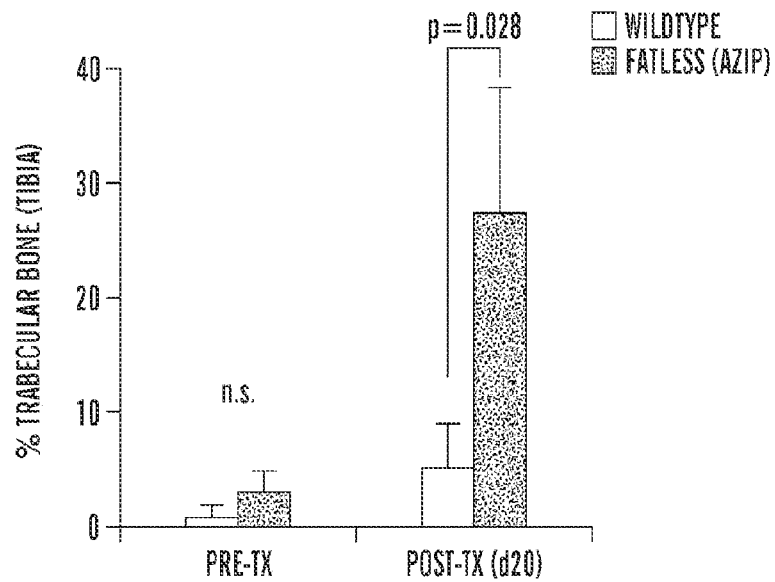
Figure 3C:
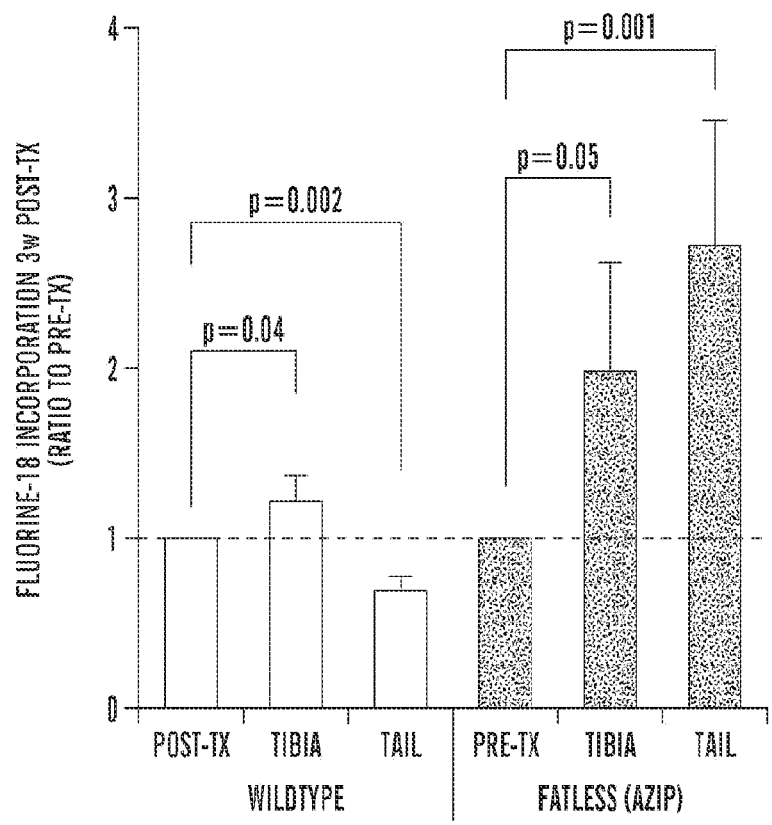

FIGS. 3a-c: Ablation of the hematopoietic compartment in fatless A-ZIP/F1 mice during BM transplantation induces osteogenesis.

Analysis of mice transplanted as in FIG. 2. 3a. Average trabecular bone density of normalized to a density standard (phantom). 3b. Percentage BM space occupied by trabecular bone 20 days after transplantation. 3c. MicroPET analysis (Positron Emission Tomography) pre/post-transplant. Representative mice shown at three different time points (3-4 analyzed per group). Dark areas indicate NaF-18 uptake in regions of active bone deposition (red arrowheads). 3d. Quantification of mean NaF-18 uptake in tibiae and proximal tails pre/post-transplantation.

Figure 4A:
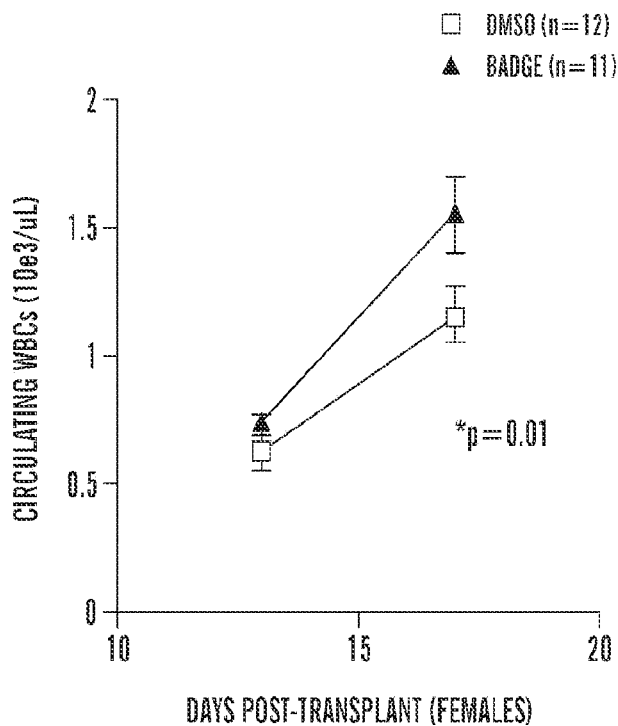
Figure 4B:
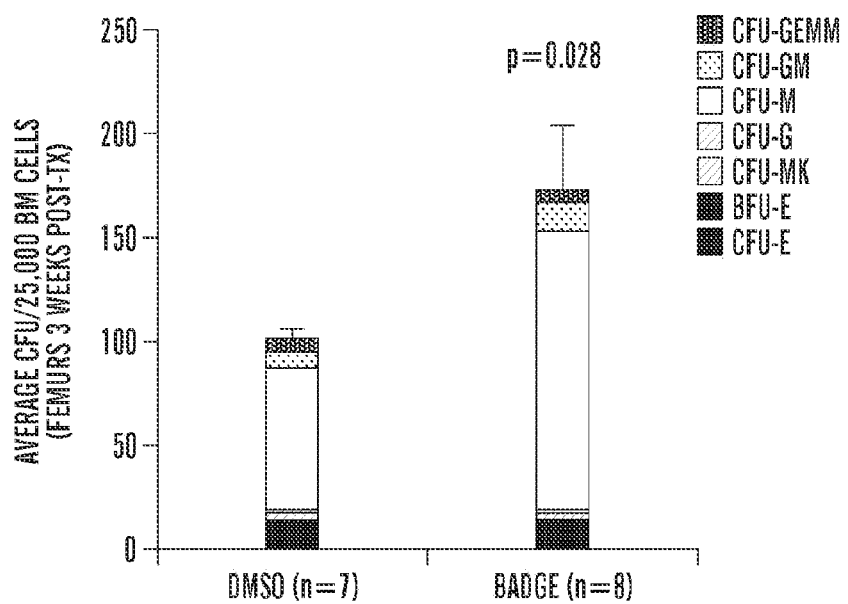

FIG. 4a-b: Pharmacological inhibition of adipocyte formation enhances BM engraftment in wild-type mice.

BM transplants were performed in wild-type female FVB mice as described for FIG. 2 except that 30 mg/kg BADGE or control vehicle (DMSO 10%) were administered through daily intra-peritoneal injections from the day prior to irradiation until day 14 post-transplant. 4a. White blood cell (WBC) counts in peripheral blood on the post-transplant period show accelerated recovery in BADGE-treated mice. 4b. Colony forming unit assay (CFU) from the recovered donor BM.

Figure 5:
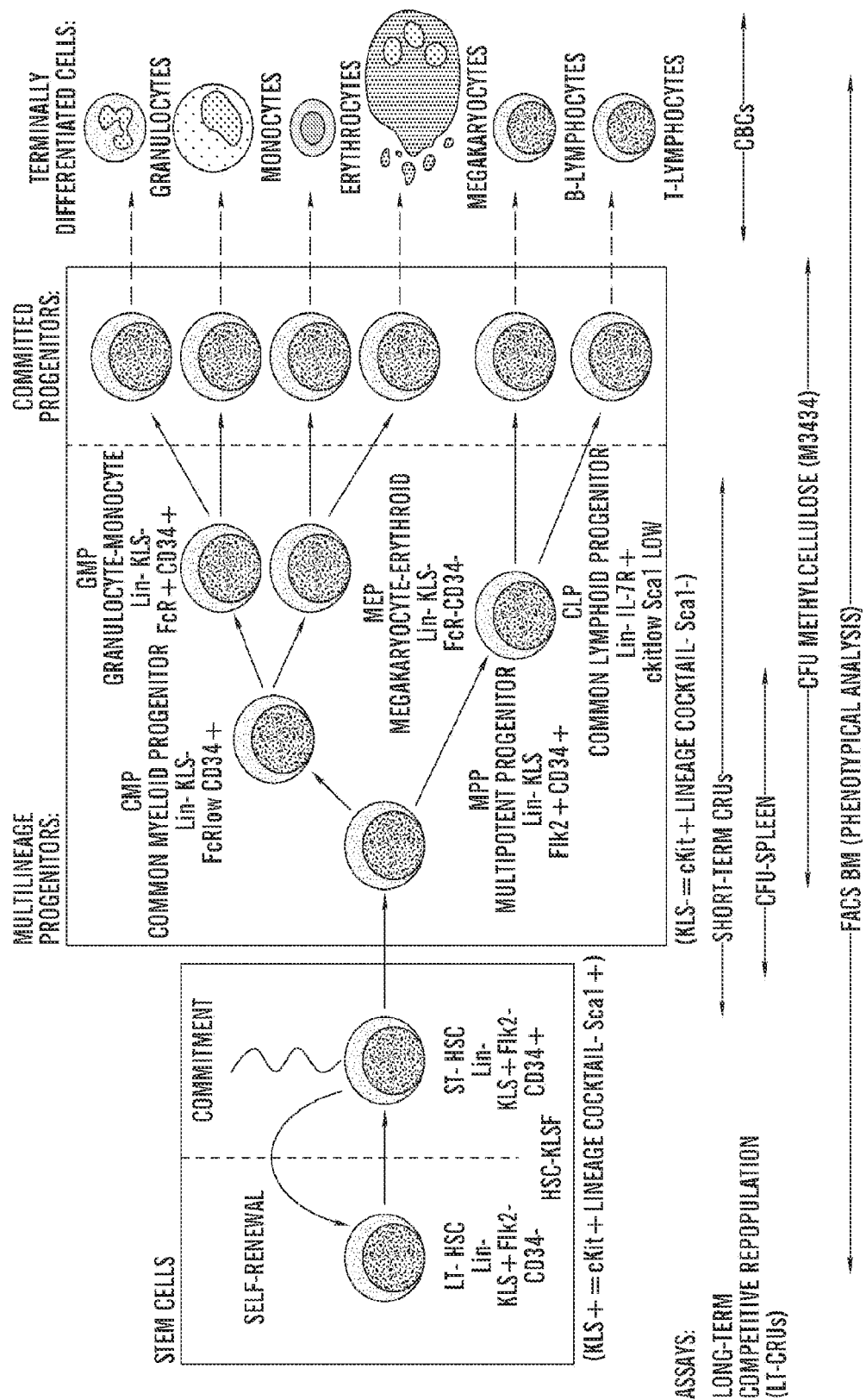

FIG. 5: Schematic diagram of the hematopoietic progenitor hierarchy and the surface markers or functional assays used to identify the different progenitor compartments.

Lin-, lineage negative; PROG, progenitors; HSC, hematopoietic stem cells (ckit+Lin-Sca1+Flk2–); LT-HSC, long-term HSC (CD34–); ST-HSC, short-term HSC(CD34+); MPP, multipotent progenitors; CMP, common myeloid progenitors; GMP, granulocyte-monocyte progenitors; MEP, megakaryocyte-erythrocyte progenitors. CFU, colony forming unit; GEMM, granulocyte-erythroid-monocyte-megakaryocyte mixed CFU; GM, granulocyte-monocyte CFU; M, monocyte CFU; G, granulocyte CFU; Mk, megakaryocyte CFU; E+BFU, erythroid CFU and erythroid blast forming unit.

Figure 6B:
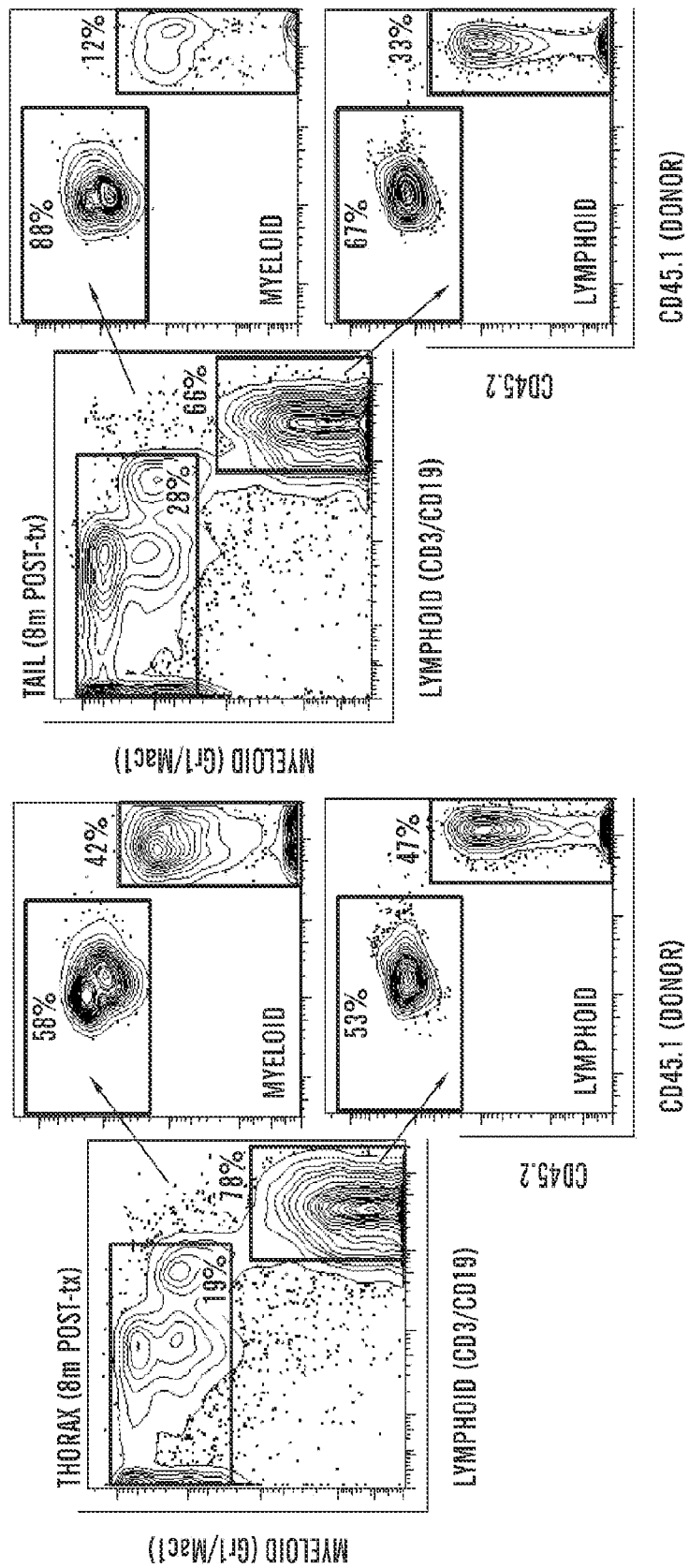
Figure 7C:
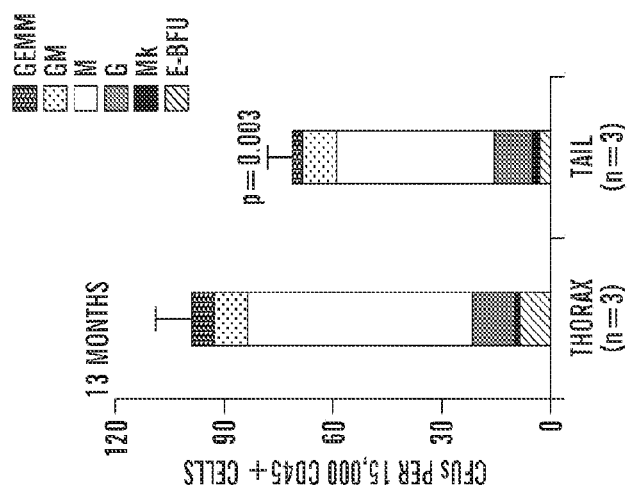
Figure 7B:
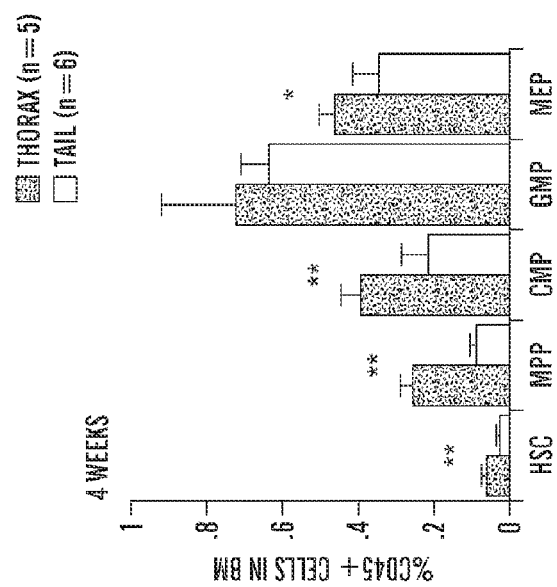
Figure 7A:
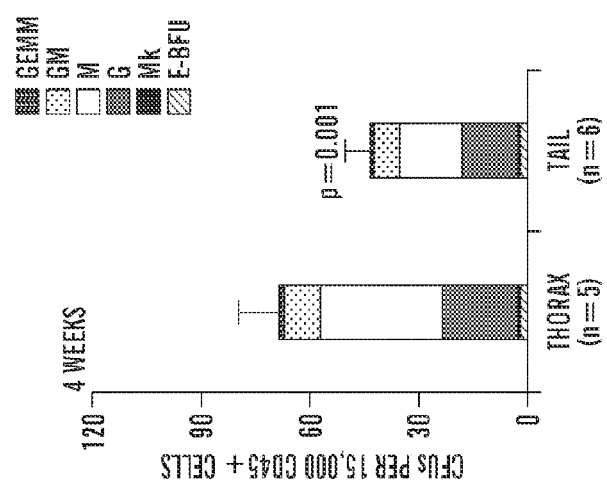
Figure 7D:
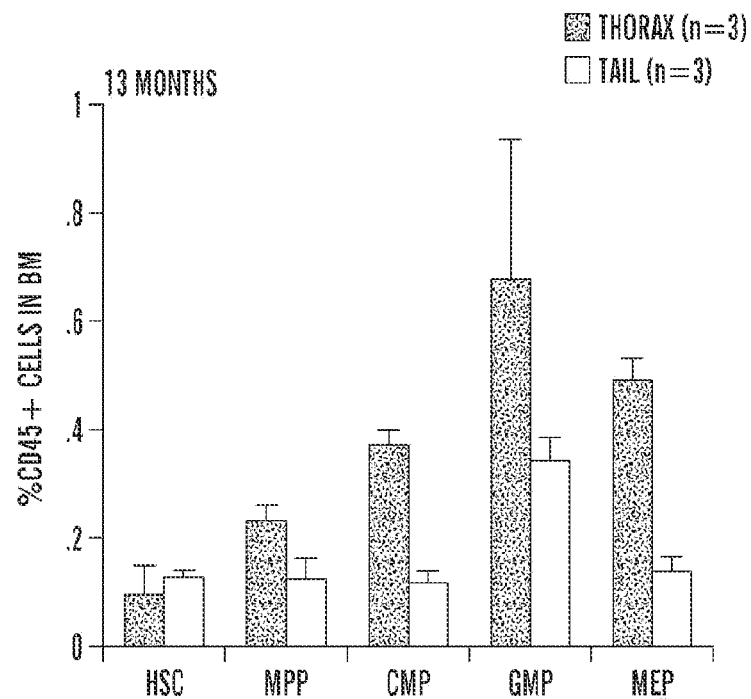
Figure 7E:
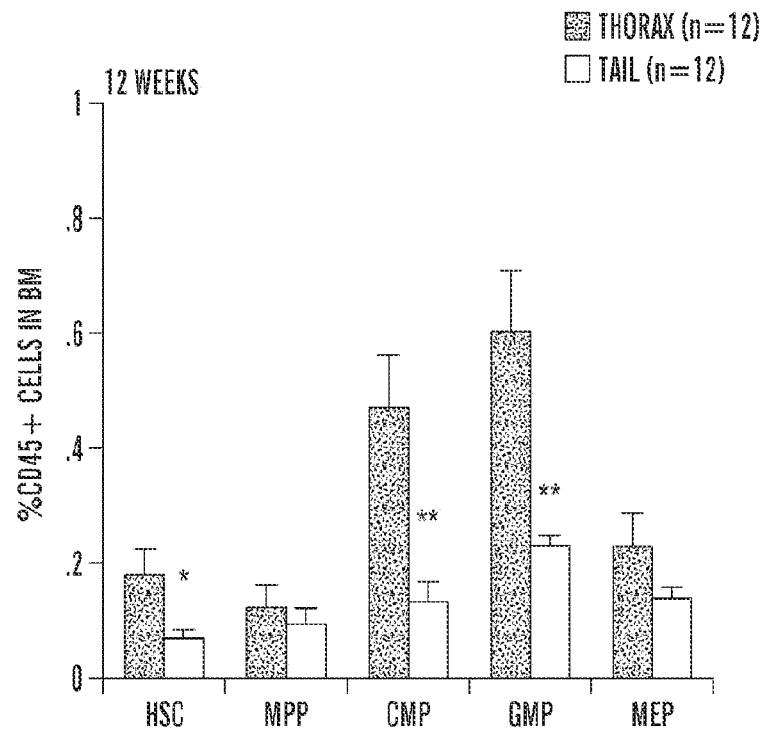

FIGS. 6a-b: Adipocyte-rich tail bone marrow contains reduced number of hematopoietic progenitors during homeostasis.

6a. Flow cytometry analysis and relative frequencies of hematopoietic progenitors within the thoracic (top) and tail (bottom) BM±STD. Lin-, lineage negative; PROG, progenitors; HSC, hematopoietic stem cells (ckit+Lin-Sca1+Flk2–); CMP, common myeloid progenitors; GMP, granulocyte-monocyte progenitors; MEP, megakaryocyte-erythrocyte progenitors. 6b. Flow cytometry analysis for myeloid (Gr1.Mac1) and lymphoid (CD3/CD19) engraftment in peripheral blood after competitive transplantation of CD45.1 donor thorax or tail BM (250,000 cells) against 250,000 CD45.2 competitor cells from femoral BM. Representative plots are shown for the 8-month post-transplant time-point presented in FIG. 1d.

FIGS. 7a-e: Adipocyte-rich bone marrow contains reduced number of hematopoietic progenitors regardless of age and location.

7a. Frequency of CFUs and 7b. phenotypic FACS analysis of thoracic versus tail BM in young, 4 week-old mice. HSC, hematopoietic stem cells (ckit+Lin-Sca1+Flk2); MPP, multipotent progenitors; CMP, common myeloid progenitors; GMP, granulocyte-monocyte progenitors; MEP, megakaryocyte-erythrocyte progenitors. 7c. Frequency of CFUs and 7d. phenotypic FACS analysis of thoracic versus tail BM in old, 13 month-old mice. 7e. Phenotypic FACS analysis of thoracic versus distal tibia BM in adult, 12 week-old mice.

Figure 8A:
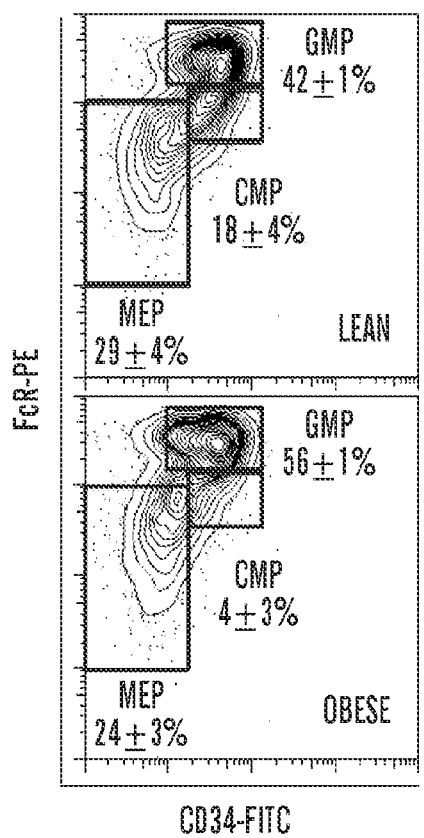
Figure 8B:
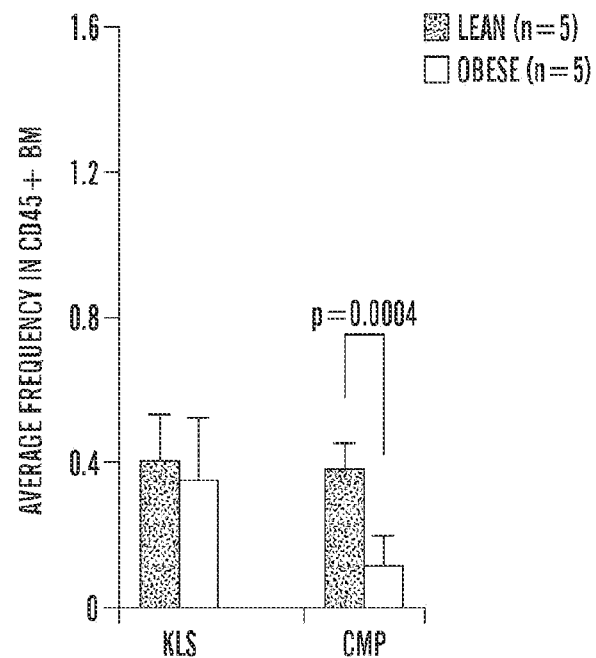
Figure 8C:
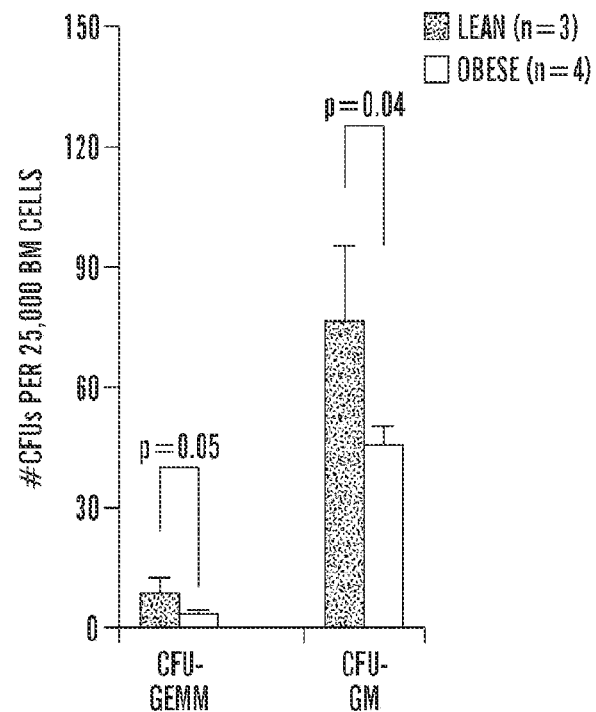

FIGS. 8a-c: Adipocyte-rich bone marrow from obese mice also contains reduced number of hematopoietic progenitors.

8a. Representative FACS plot (gated on CD45+Lin-ckit+Sca1–) and 8b. relative frequency of hematopoietic progenitors in the femoral ob/ob mice showing a deficit in CMPs, which translates functionally to a significant decrease in the ability to form CFU-GEMMs and CFU-GMs, as shown in 8c.

Figure 9A:
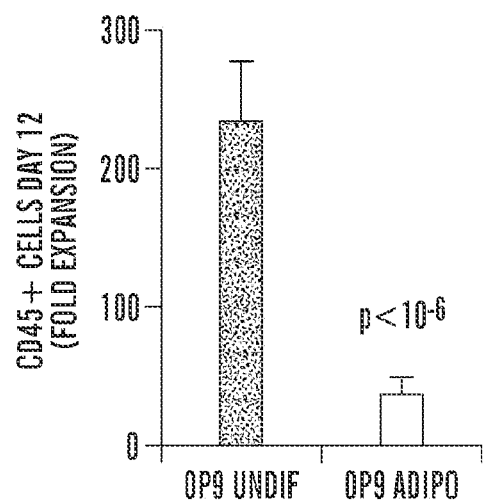
Figure 9B:
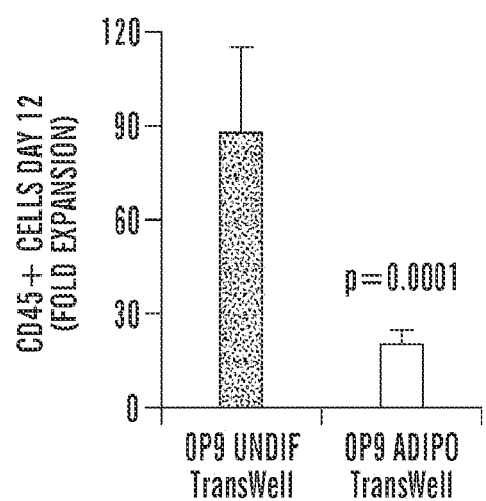

FIG. 9a-b: BM-derived adipocytes are sufficient to reduce the expansion of hematopoietic cells on stromal co-cultures in vitro both in contact cultures and trans-well assays.

Fold expansion of CD45+ cells after 8 days is indicated in 9a. demonstrating that, also in vitro, BM-derived adipocytes can prevent hematopoietic expansion. 9b. Proliferation of KLS cells in OP9 supportive stroma was also compromised when OP9-derived adipocytes were present in the lower chamber of a trans-well assay, indicating that soluble adipocyte-derived inhibitors of hematopoiesis are present in the culture.

Figure 10A:
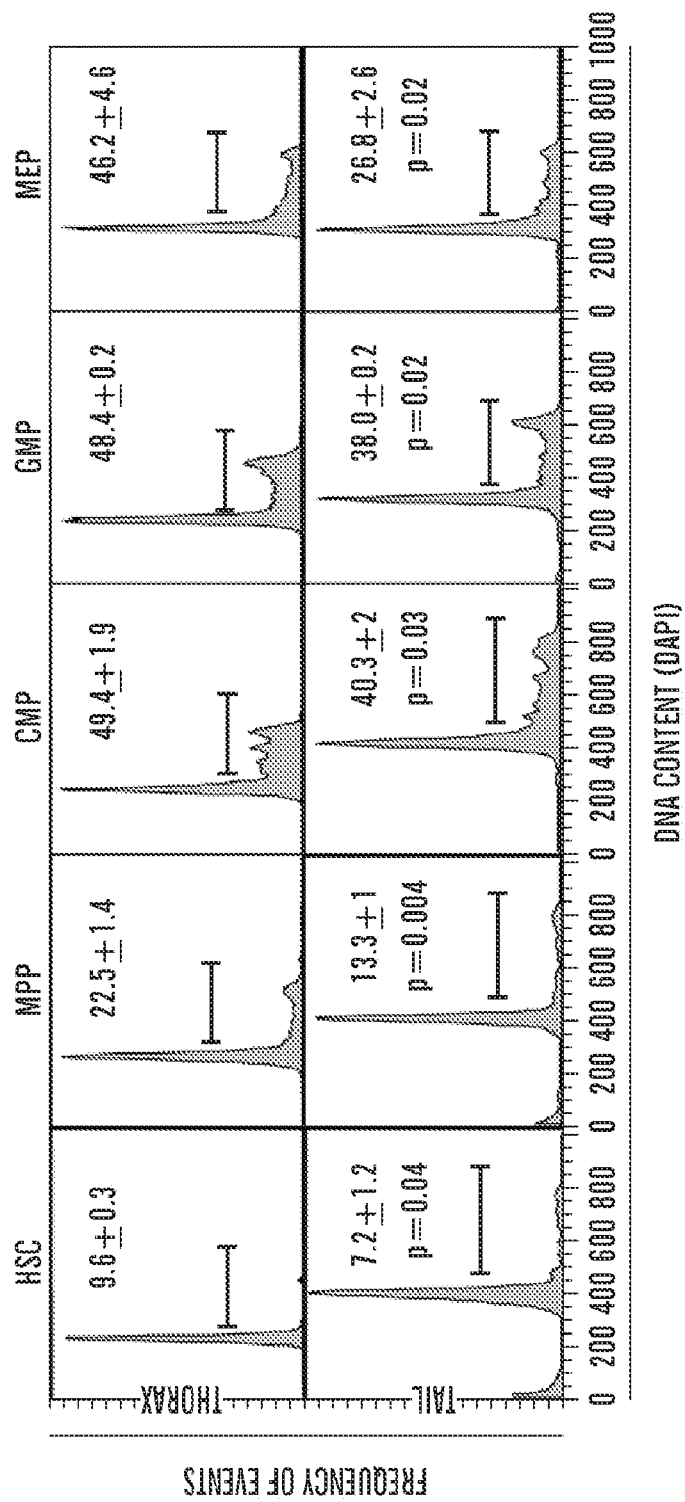
Figure 10B:
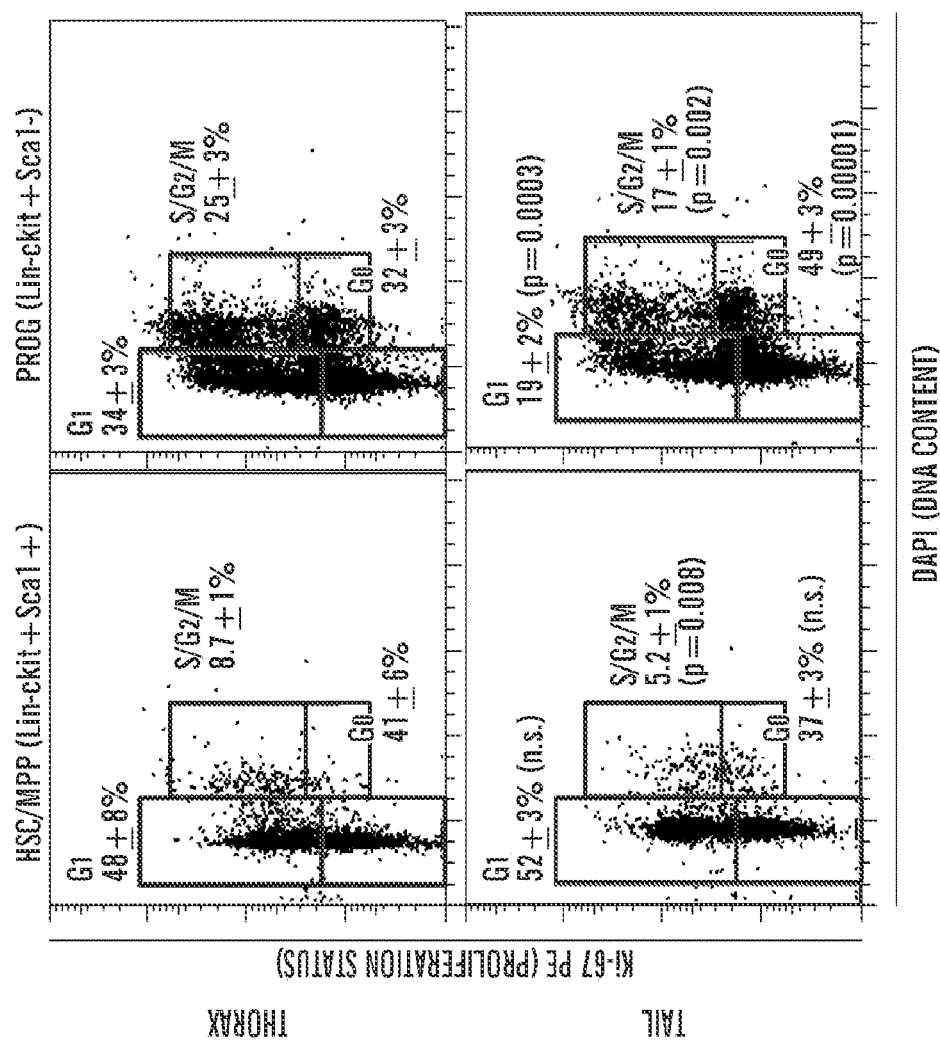

FIGS. 10a-b: Hematopoietic stem cells and progenitors present reduced cycling capacity in adipocyte-rich tail bone marrow during homeostasis.

10a. Cell cycle analysis DAPI DNA stain in combination with multicolour FACS analysis. Thorax and tails from 4 different animals were pooled for each of three experiments. Numbers indicate average % of cells in S/G2/M transition±SEM. 10b. Ki-67 versus DAPI cell cycle analysis FACS plots in thorax (top) and tail (bottom) BM showing reduced cycling but similar G0/G1 distribution in the KLS compartment (ckit+Lin-Sca1+, which contains HSCs and MPPs) and increased G0/G1 ratio within the progenitor fraction (ckit+Lin-Sca1–, which contains CMP, GMP and MEPs) from the adipocyte-rich tail. Note that PROG plots contain a Ki67-DAPI+ population (low ploidy megakaryocytes) that have been excluded from the analysis. Representative plots from 4 independent pools of 3 mice each; percentages indicate average±STD. HSC, hematopoietic stem cells (ckit+Lin-Sca1+Flk2); MPP, multipotent progenitors; CMP, common myeloid progenitors; GMP, granulocyte-monocyte progenitors; MEP, megakaryocyte-erythrocyte progenitors, KLS, ckit+Lin-Sca1+, PROG, ckit+Lin-Sca1–.

Figure 11:
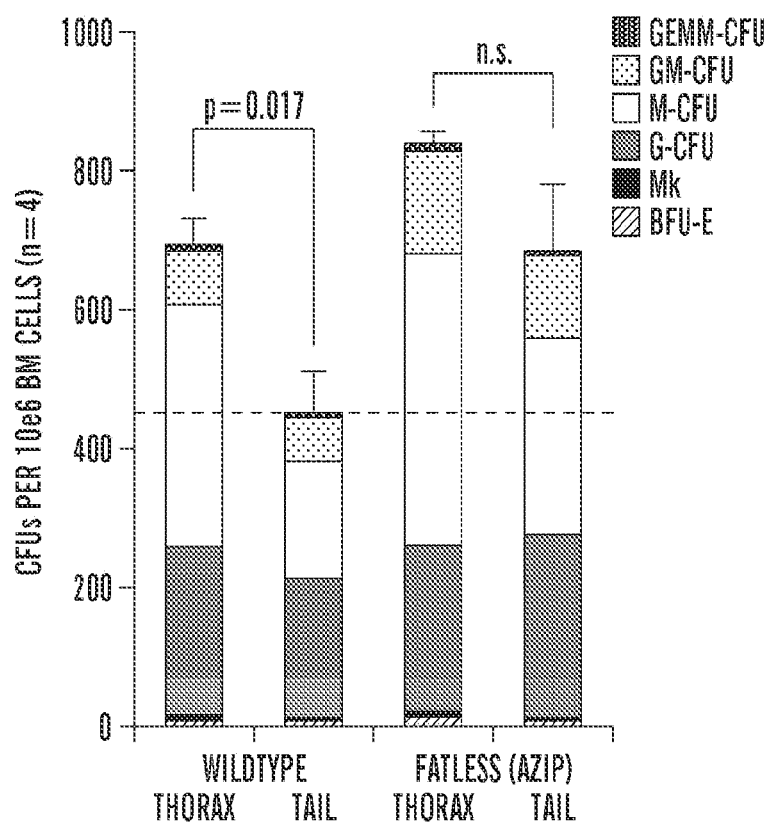

FIG. 11: Absence of adipocytes in A-ZIP/F1 "fatless" mice rescues hematopoiesis in tail BM.

Thorax and tail BM colony forming units (CFU) from wildtype (left) and A-ZIP/F1 fatless (right) littermates.

FIGS. 12a-d: The lack of bone marrow adipocytes in fatless mice enhances hematopoietic progenitor expansion and post-transplant recovery, but does not cause hematopoietic advantage prior to BM transplantation.

12a. Leukocyte and erythrocyte counts in peripheral blood of 5-7 week-old wild-type vs. A-ZIP/F1 fatless mice (HemaVet, Drew Scientific) and 12b. competitive repopulation with BM from pre-transplant wild-type vs. A-ZIP/F1 fatless mice showing no competitive hematopoietic advantage in the pre-transplant A-ZIP/F1 mice in short-term (top) or long-term (bottom) engraftment. 12c. Engraftment of wildtype CD45.2+BM into CD45.1+ wildtype or fatless mice is equivalent in the primary transplants, indicating that the residual radio-resistant A-ZIP BM does not explain the accelerated recovery from BM transplantation in fatless A-ZIP/F1 mice. 12d. Absolute number of CFUs per leg (femur+tibia) in post-transplant wild-type vs. A-ZIP/F1 mice during the first 3 weeks post-transplant; n=2-3 per time-point.

Figure 13:
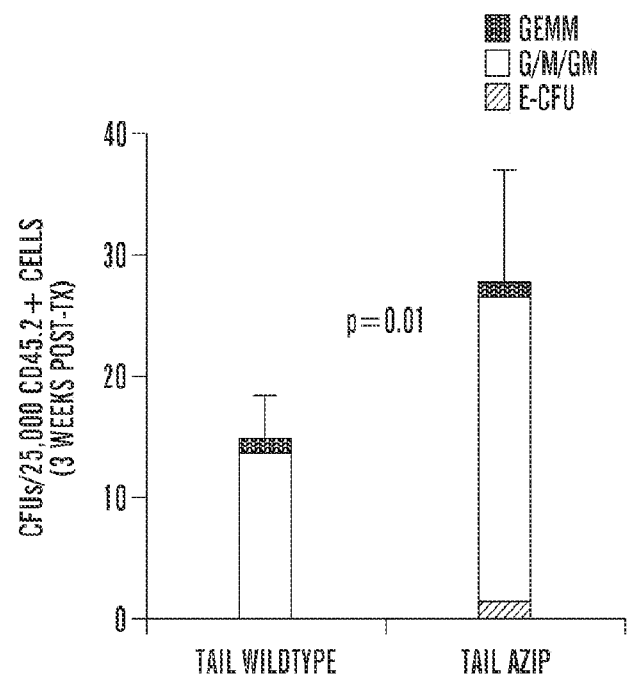

FIG. 13: The lack of bone marrow adipocytes post-irradiation in fatless mice enhances hematopoietic progenitor expansion also in the tail.

Colony forming units (CFU) in the tail BM of wildtype vs. fatless A-ZIP/F1 mice 3 weeks post-transplant.

Figure 14:
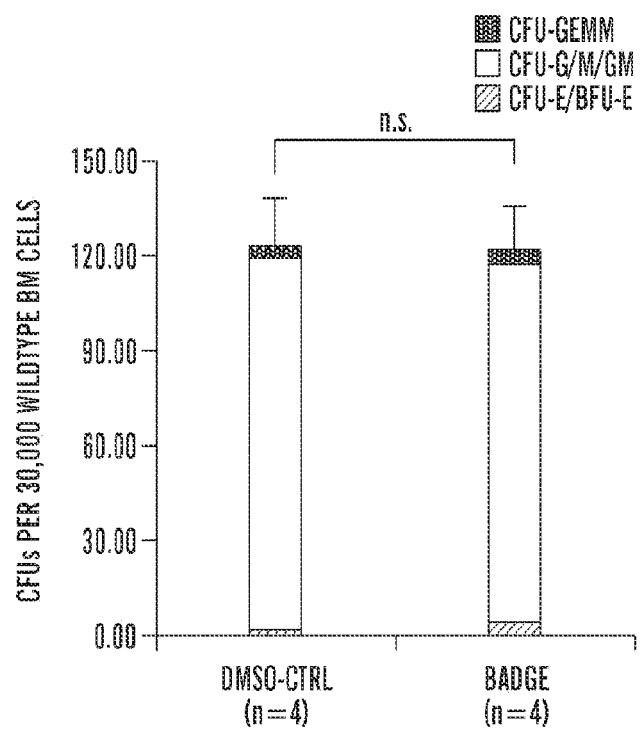

FIG. 14: PPARγ inhibitor BADGE does not cause direct hematopoietic expansion in vitro.

14a. Wildtype BM was plated in the presence of BADGE 30 mg/kg, or DMSO vehicle control (0.5 μL/mL). No difference was observed in the ability to form CFUs after 8-10 days, indicating that BADGE does not have a direct effect in hematopoietic progenitor expansion.

Figure 15:
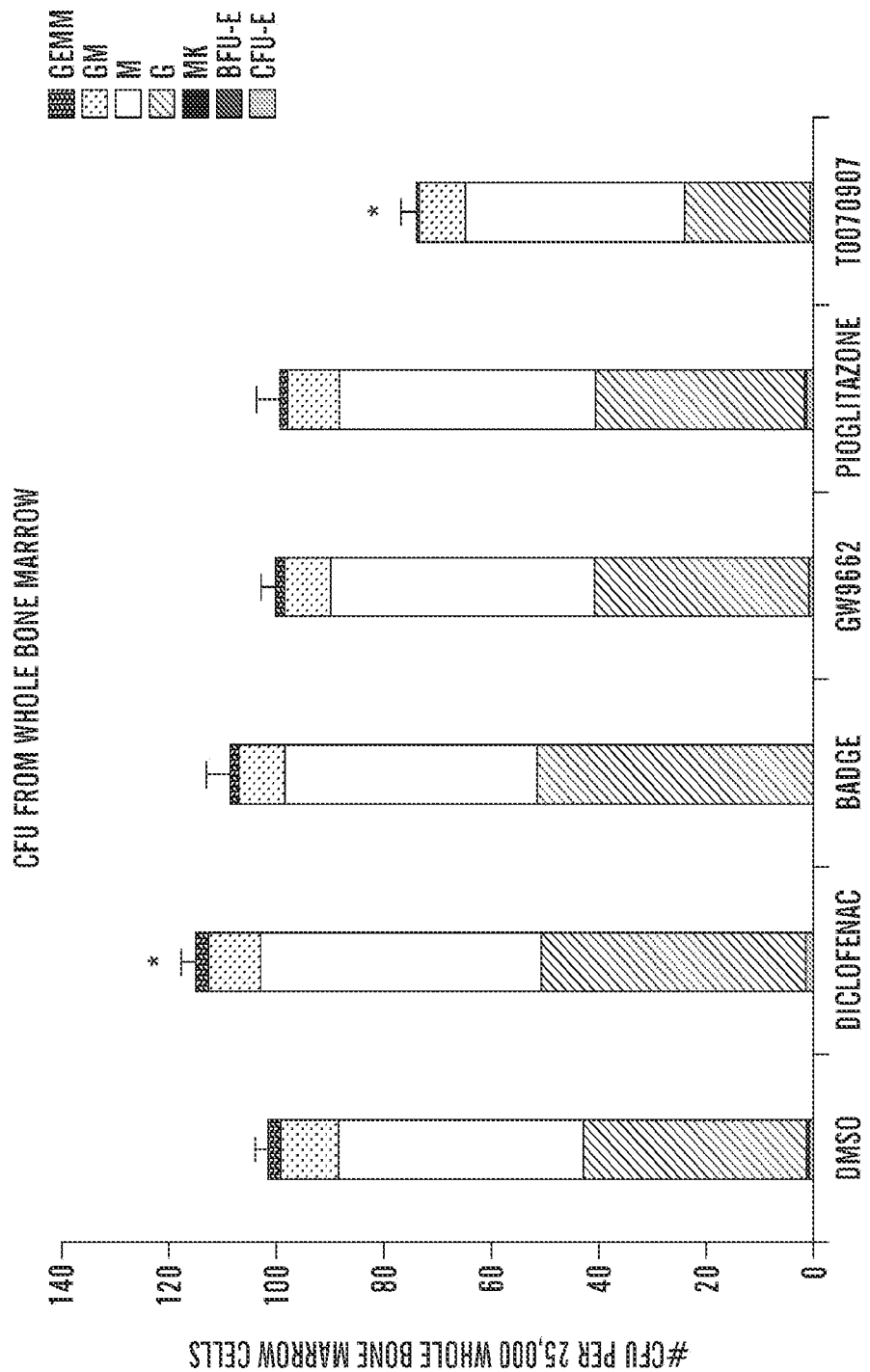

FIG. 15: Progenitor activity in the presence of various compounds. To test additional PPAR gamma inhibitors for toxicity or adipocyte-independent enhancement of progenitor expansion, hematopoietic colony formation was measured in vitro. 15a. Progenitor activity was measured by formation of hematopoietic colonies in methylcellulose (M3434) from whole bone marrow collected from the DBA/1J mouse strain. Cells were plated in 3 ml M3434 along with 1.5 μL of the working concentration of each compound. This approach was consistent with that used in the Examples section (see also e.g., Naveiras et al., (2009) Nature 469:259-263) to measure toxicity or enhancement of progenitor activity. An equal or greater number of hematopoietic colonies form in the presence of four of the compounds tested. The T0070907 compound resulted in the growth of fewer colonies relative to the vehicle control. *P-value<0.001, Student's t-test, N=2.

Figure 16:
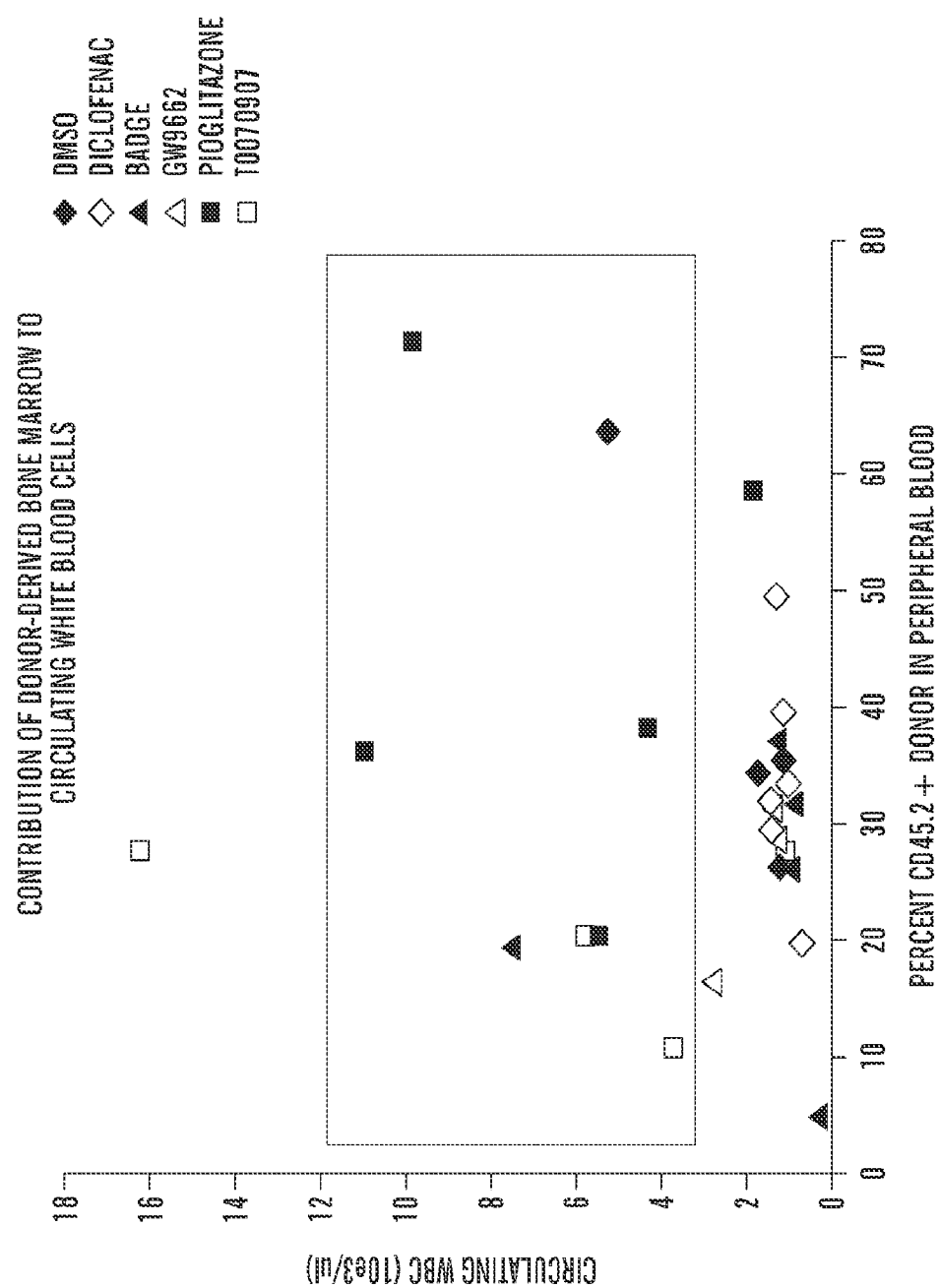

FIG. 16: Contribution of donor-derived bone marrow to circulating white blood cells Various PPAR gamma antagonists and modulators were administered to mouse transplant recipients to identify additional compounds that would increase numbers of circulating white blood cells during the post-transplantation period. 16a. Engraftment of transplanted bone marrow cells and numbers of circulating white blood cells were measured during the post-transplantation period at 18 days. Five 6-7 week old female CD45.1 FVB/NJ recipients received 11 GY irradiation, followed by immediate transplantation of 200,000 CD45.2 DBA/1J whole bone marrow cells. Compounds were administered daily, beginning the day before radiation treatment and resuming on the day following transplantation of the cells. Each point represents a single transplant recipient. The box depicts the normal range of circulating white blood cells for the DBA/1J mouse strain.

Figure 17:
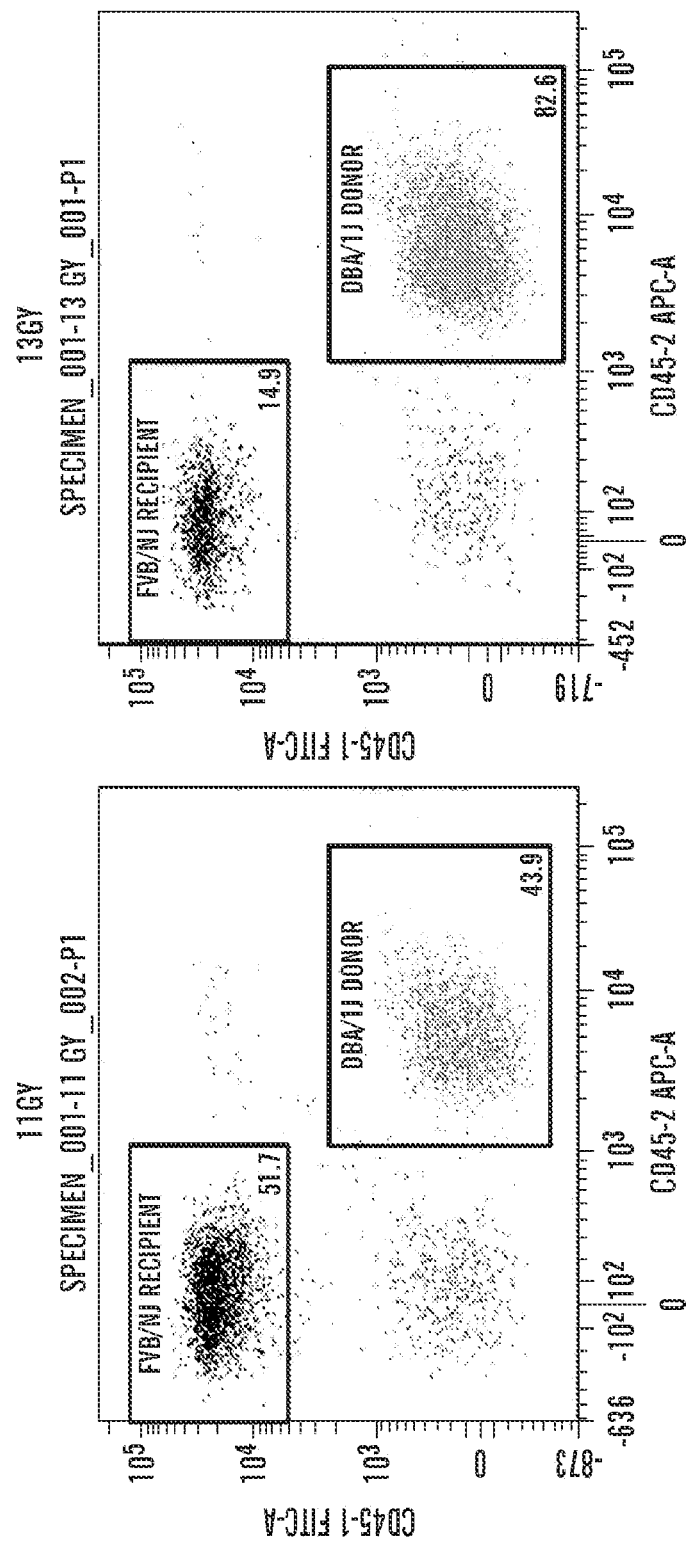

FIG. 17a-b: Radiation exposure was optimized for a cohort of FBV/NJ females age-matched to recipients for the ongoing round of compound treatments. It was observed that in the first transplantation screen (using 11 GY irradiation) a substantial amount of the marrow in the CD45.1 FBV/NJ recipient mice was radioresistant, making CBC levels less accurate. It was determined from irradiation at 11 GY, 13, GY, and 15 GY that exposure to 13 GY maximized ablation of host marrow, without causing lethal radiation poisoning (n=2 at each dose). Representative FACS plots from 3 weeks post-transplantation depicted below: 17a. the left plot (11GY) shows that 51.7% of peripheral blood is derived from radioresistant FVB/NJ marrow, whereas the right plot (13 GY) demonstrates a drop to 14.9% of circulating cells that are radioresistant. Mice exposed to 15GY died of excessive radiation prior to 3 weeks.

DETAILED DESCRIPTION

Infiltration of adipocytes into red bone marrow occurs in patients that have received irradiation and/or chemotherapy and in patients with bone marrow aplasia. Embodiments of the invention are based on the observation that the presence of adipocytes in fatty marrow reduces hematopoiesis, is associated with a reduced number of hematopoietic progenitor cells, and hinders hematopoietic progenitor cell expansion. Applicants have further discovered that pharmacological antagonism of adipogenesis enhances hematopoietic recovery (e.g., short term progenitor cell engraftment).

Described herein are methods useful for improving engraftment of hematopoietic cells in an individual following hematopoietic progenitor cell transplantation (e.g., via bone marrow or cord blood transplantation). Methods for increasing hematopoietic progenitor cell proliferation in individuals with bone marrow aplasia are also described. The methods involve administering an agent that inhibits adipogenesis, adipocyte growth, adipocyte differentiation and/or adipocyte proliferation. The methods described herein are also useful for promoting osteogenesis and hematopoiesis in a subject.

Hematopoietic Progenitor Cells

Hematopoietic progenitor cells, as the term is used herein, are capable of producing all cells types in the hematopoietic lineage, but are not capable of long-term self-renewal. Thus, hematopoietic progenitor cells can restore and sustain hematopoiesis for three to four months (Marshak, D. R., et al. (2001). *Stem cell biology*, Cold Spring Harbor, N.Y.: Cold Spring Harbor Laboratory Press) and are important for recovery in the period immediately following a hematopoietic progenitor cell transplant in an individual. Hematopoietic progenitor cells useful for transplantation can be obtained from a variety of sources including, for example, bone marrow, peripheral blood, and umbilical cord blood.

Bone marrow can be obtained by puncturing bone with a needle and removing bone marrow cells with a syringe (herein called "bone marrow aspirate"). Hematopoietic progenitor cells can be isolated from the bone marrow aspirate prior to transplantation by using surface markers specific for hematopoietic progenitor cells, or alternatively whole bone marrow can be transplanted into an individual to be treated with the methods described herein.

Hematopoietic progenitor cells can also be obtained from peripheral blood of a progenitor cell donor. Prior to harvest of the cells from peripheral blood, the donor is treated with a cytokine, such as e.g., granulocyte-colony stimulating factor, to promote cell migration from the bone marrow to the blood compartment. Cells can be collected via an intravenous tube and filtered to isolate white blood cells for transplantation. The white blood cell population obtained (i.e., a mixture of stem cells, progenitors and white blood cells of various degrees of maturity) can be transplanted as a heterogeneous mixture or hematopoietic progenitor cells can further be isolated using cell surface markers known to those of skill in the art.

Hematopoietic progenitor cells and/or a heterogeneous hematopoietic progenitor cell population can also be isolated from human umbilical cord and/or placental blood.

Exemplary Cell surface markers suitable for isolating a desired hematopoietic stem cell type are provided herein in Table 1.

TABLE 1

Cell surface markers to identify different progenitor compartments

| Progenitor Cell Type | Abbreviation | Cell Surface Markers |
|---|---|---|
| short term hematopoietic stem cells | ST-HSCs | Lin− KLS+ Flk2− CD34+ |
| common myeloid progenitor cells | CMPs | Lin− KLS− FcR$_{low}$ CD34+ |
| granulocyte-monocyte progenitor cells | GMPs | Lin− KLS− FcR+ CD34+ |
| megakaryocyte-erythroid progenitor cells | MEPs | Lin− KLS− FcR− CD34− |
| multipotent progenitor cells | MPPs | Lin− KLS+ Flk2+ CD34+ |

Diseases of the Hematopoietic System

Hematopoietic progenitor cells can be transplanted to regenerate hematopoietic cells in an individual having a disease of the hematopoietic system. Such diseases can include, but are not limited to, cancers (e.g., leukemia, lymphoma), blood disorders (e.g., inherited anemia, inborn errors of metabolism, aplastic anemia, beta-thalassemia, Blackfan-Diamond syndrome, globoid cell leukodystrophy, sickle cell anemia, severe combined immunodeficiency, X-linked lymphoproliferative syndrome, Wiskott-Aldrich syndrome, Hunter's syndrome, Hurler's syndrome Lesch Nyhan syndrome, osteopetrosis), chemotherapy rescue of the immune system, and other diseases (e.g., autoimmune diseases, diabetes, rheumatoid arthritis, system lupus erythromatosis).

Agents that Alter Adipocyte Metabolism

Any agent that alters adipocyte metabolism in such a manner to inhibit adipogenesis, inhibit adipocyte growth, inhibit proliferation and/or inhibit differentiation can be used with the methods described herein. The agent may act on an adipocyte, a pre-adipocyte, an adipocyte progenitor cell, or a mesenchymal stem cell. It is preferred that an agent is selective for a metabolic pathway in an adipocyte (or adipocyte precursor cell), such that the metabolic pathways of other cell types (e.g., hepatocytes, cardiac myocytes etc) is substantially unaffected. Exemplary agents useful for inhibiting adipocyte proliferation and/or differentiation in bone marrow following bone marrow transplantation include, but are not limited to, inhibitors of PPARγ, inhibitors of ap2/FABP4, and inhibitors of 11 beta-hydrosteroid dehydrogenase.

An agent can be tested for an inhibitory effect on adipocyte proliferation and/or adipocyte proliferation by using any in vitro proliferation assay or adipocyte differentiation assay known to those of skill in the art. Such assays can be performed in an immortalized adipocyte or pre-adipocyte cell line, such as e.g., 3T3-L1 adipocytes. Differentiation of adipocytes can be induced by adding IBMX, dexamethasone, and insulin to the cell culture conditions. An agent can be tested for inhibition of adipocyte differentiation under these, or other differentiation conditions, known to those of skill in the art.

In general, an agent is considered to an inhibitor of adipogenesis, adipocyte growth, adipocyte proliferation, or adipocyte differentiation if the growth and/or differentiation of an adipocyte is reduced by at least 10% in the presence of such an agent, as assessed by an in vitro adipocyte proliferation and/or differentiation assay. It is preferred that the reduction in adipogenesis, or reduction in adipocyte growth, or reduction in adipocyte proliferation or reduction in adipocyte differentiation is at least 20%, at least 30%, at least 40%, at least 50%, at least 60%, at least 70%, at least 80%, at least 90%, at least 95%, at least 99%, or even 100% (i.e., absent) in cells treated with an agent that alters adipocyte metabolism compared to untreated adipocyte cells. In some embodiments, the agent that "alters adipocyte metabolism" can also promote cell death of an adipocytic cell (i.e., greater than 100% reduction in proliferation or growth).

PPARγ Inhibitors

PPARγ is a ligand-regulated transcription factor of the nuclear hormone receptor superfamily that is expressed primarily in adipose tissue. Biological processes known to be modulated by PPARγ include, for example, cell differentiation to produce lipid accumulating cells, regulation of insulin sensitivity and blood glucose levels, hypoglycemia/hyperinsulinism, macrophage differentiation, inflammatory response, carcinogenesis, hyperplasia, and adipocyte differentiation.

The activity of a PPARγ antagonist can be determined using a GAL4 chimeric receptor transcriptional assay, as described by Berger et al, Journal of Biological Chemistry, Vol 274, 6718-6725 (1999) or alternatively by using the PPAR-CBP HTRF assay, as described by Zhou, et al, Molecular Endocrinology, Vol. 12, 1594-1604 (1998) (herein incorporated by reference in its entirety). The activity of a PPARγ antagonist can also be measured using a 3T3-L1 pre-adipocyte cell differentiation assay, as described by Berger et al, Journal of Biological Chemistry, Vol 274, 6718-6725 (1999).

Some non-limiting examples of PPARγ inhibitors include bisphenol-A-diglycidyl-ether (BADGE; available commercially form Sigma/Fluke), 2-chloro-5-nitro-N-4-pyridinyl-benzamide (T0070907; available commercially from Cayman; Axxora Biochemicals, Bingham, Nottingham, UK), 2-chloro-5-nitrobenzanilide (GW9662; available commercially from Cayman; Lea, M. A. et al (2004) *Anticancer Res* 24(5A):2765-71), (4-chlorophenyl)-(diemethoxyphosphinyl)-methyl-phosphoric acid-dimethyl ester (mifobate; SR-202), 2-((5,5,8,8-tetramethyl-5,6,7,8-tetrahydro-2-naphthyl)carbonyl)benzoic acid (LG 100641), propanamide, 2,2-dimethyl-N-[5-nitro-3-(2-propen-1-yl)-2(3H)-thiazolylidene] (PD068235; Camp, H S et al (2001) *Endocrinology* 142(7):3207-13); pioglitazone; diclofenac (Lea, M A et al. (2004), supra); MK886 (available commercially from Calbiochem; De Gottardi, A et al (2008) *Gut* 57(1):137); (2-thiophenecarboxylic acid, 3-[[[2-methoxy-4-(phenylamino)phenyl]amino]sulfonyl]-, methyl ester (GSK0660; Shearer, B G (2008) *Mol Endocrinol* 22(2):523-9); benzoic acid, 2-[(5,6,7,8-tetrahydro-5,5,8,8-tetramethyl-2-naphthalenyl)carbonyl]-) (LG100641; Mukherjee R, et al (2000) *Mol Endocrinol* 14(9):1425-33); benzoic acid, 4-(7,8,9,10-tetrahydro-5,7,7,10,10-[entamethyl-2-nitro-5H-benzo[b]naphtho[2,3-e][1,4]diazepin-12-yl)-) (HX531; Bourhis, E et al. (2009) *Psychopharmacology (Berl)* 202(4):635-48); ((4-2((2S,5S)-5-2(-(bis(phenylmethyl)amino)-2-oxoethyl)-2-heptyl-4-oxo-3-thiazolidinyl)butyl)-benzoic acid) (GWO072).

Dosage ranges for agents are discussed in the Dosage and Administration section herein and can be modified as necessary by one of skill in the art. In one embodiment, the agent 2-chloro-5-nitro-N-4-pyridinyl-benzamide (T00700907) can be administered by intraperitoneal injection with a starting dosage of 1 mg/kg body weight.

In another embodiment, the agent 2-chloro-5-nitrobenzanilide (GW9662; available from Cayman Chemicals, Ann Arbor, Mich.) can be administered by intraperitoneal injection with a starting dosage of 1 mg/kg body weight. In one embodiment, the agent dimethyl alpha-(dimethoxyphosphinyl)-p-chlorobenzyl phosphate (SR-202; available from Tocris Biosciences, Ellisville, Mo.) can be administered orally at 400 mg/kg.

ap2/FABP4 Inhibitors

Fatty-acid-binding proteins (FABPs) are a family of carrier proteins that facilitate the intracellular transport of fatty acids and other lipophilic substances (e.g., eicosanoids and retinoids). aP2/FABP4 is a carrier protein for fatty acids that is primarily expressed in adipocytes and macrophages and promotes adipocyte differentiation.

An exemplary inhibitor of ap2/FABP4 is BMS309403 (available from Bristol-Meyers Squibb, New York, N.Y.), which can be administered using intraperitoneal injection. Other inhibitors of ap2/FABP4 include, but are not limited to, N-benzyl-hexahydrocyclohepta[b]indole (commercially available from Biovitrum; Barf, T et al (2009) *Bioorg Med Chem Lett* 19(6):1745-8); and 1,3-oxazinan-2-one derivatives (commercially available from Vitae Pharmaceuticals Inc., USA).

11 Beta-Hydroxysteroid Dehydrogenase Inhibitors

11-β hydroxysteroid dehydrogenase is an enzyme that interconverts hormonally inactive cortisone to cortisol in a bidirectional manner. The production of cortisol in adipose tissue stimulates adipogenesis and lipolysis. Inhibition of 11-β hydroxysteroid dehydrogenase has been shown to inhibit adipogenesis of human adipocytes (Bujalska, I. J., et al (2008) *J Endocrinol* 197(2):297-307).

Non-limiting examples of inhibitors of 11-β hydroxysteroid dehydrogenase include PF-877423 (available from Pfizer, New York, N.Y.; can be administered orally); BVT.2733 (Alberts P. et al. (2002) *Diabetologia* 45(11):1528-32); 4-thiazoleacetamide, 2-[[(3-chloro-2-methylphenyl)sulfonyl]amino]-N,N-diethyl-2-[2-[[3-Chloro-2-methylphenyl_sulfonyl]amino]-1,3-thiazol-4-yl]-N,N-diethylacetamide (BVT.14225; Barf, T, et al (2002) *J Med Chem* 45(18):3813-5); and trifluoromethyl thiazolone (Jean D J et al (2007) *J Med Chem* 50(3):429-32).

Dosage and Administration

In one aspect, the methods described herein provide a method for enhancing engraftment of hematopoietic progenitor cells following a bone marrow transplant in a subject. In one embodiment, the subject can be a mammal. In another embodiment, the mammal can be a human, although the invention is effective with respect to all mammals. The method comprises administering to the subject an effective amount of a pharmaceutical composition comprising an agent that alters adipocyte metabolism in a pharmaceutically acceptable carrier. The dosage range for the agent depends upon the potency, and are amounts large enough to produce the desired effect e.g., an increase in the efficiency and/or rate of hematopoietic progenitor cell engraftment. The dosage should not be so large as to cause adverse side effects. Generally, the dosage will vary with the age, condition, and sex of the patient and can be determined by one of skill in the art. The dosage can also be adjusted by the individual physician in the event of any complication.

Generally, the dosage will vary with the type of agent used (e.g., an antibody or fragment, small molecule, siRNA, etc.), and with the age, condition, and sex of the patient. The dosage can be determined by one of skill in the art and can also be adjusted by a physician in the event of any complication. Typically, the dose will range from 0.001 mg/kg body weight to 5 g/kg body weight. In some embodiments, the dose will range from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dose range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

An agent that alters adipocyte metabolism can be given once a day, less than once a day, multiple times a day, or continuously in order to achieve a therapeutically effective dose. Administration of the doses recited above can be repeated for a limited period of time. In a preferred embodiment, the doses recited above can be administered daily for several weeks or months. The duration of treatment depends upon the subject's clinical progress and responsiveness to therapy. A therapeutically effective amount is an amount of an agent that is sufficient to produce a measurable change in engraftment efficiency or rate (see "Efficacy Measurement" below). Such effective amounts can be gauged in clinical trials as well as animal studies.

Agents useful in the invention can be administered intravenously, intranasally, orally, by inhalation, intraperitoneally, intramuscularly, subcutaneously, intracavity, and can be delivered by peristaltic means, if desired, or by other means known by those skilled in the art. In one embodiment the compounds used herein are administered orally, or intravenously to a patient following hematopoietic progenitor cell transplantation. The agent can be administered intravenously by injection or by gradual infusion over time.

In some embodiments, an agent that alters adipocyte metabolism is administered as part of a combination therapy regime. Therapeutic compositions containing at least one agent that alters adipocyte metabolism can be conventionally administered in a unit dose form. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle. A combination of more than one agent can be administered in one or more pharmaceutical compositions (i.e., together in a unit dose, such as a pill or tablet, or as two separate compositions). In one embodiment, the agents are administered separately and can be administered in an order, or at an interval of time that provides effective hematopoietic stem cell graft enhancement as directed by one of skill in the art of medicine. In addition, the agents can be administered using the same or different modes of administration.

The compositions of a combination therapy are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of each active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

An agent that alters adipocyte metabolism may be adapted for slow-release drug-eluting formats, microencapsulated PEG liposomes, or nanobeads for delivery using direct mechanical intervention with or without adjunctive techniques such as ultrasound.

Pharmaceutical Compositions

The present invention involves therapeutic compositions useful for practicing the therapeutic methods described herein. Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

Efficacy Measurement

Assessing Engraftment

Engraftment after lethal ablation of the bone marrow can be assessed by measuring hematopoietic blood cell counts; in particular white blood cell counts. Following lethal ablation, recovery of normal white blood cell counts is a functional measure of successful engraftment. In a clinical context, this can be accompanied by the measurement of cellularity in the bone marrow through serial bone marrow punctions/biopsies and/or by HLA typing of circulating white blood cells. Bone marrow aspirates can also be assessed for donor chimerism as a measure of engraftment.

All blood cell types can be indicative of engraftment, but depending on their half lives, provide a more or less sensitive measure of engraftment. Neutrophils have a very short half life (just hours in the blood), and thus are a very good measure of early engraftment. Platelets also have a short half life, but they are usually the last blood element to recover to pre-transplant levels, which may not make them suitable as a marker of early engraftment.

Thus, it is noted herein that cells useful for determining engraftment of hematopoietic progenitor cells are those that recover relatively rapidly following transplantation and have a relatively short half-life (e.g., neutrophils). In one embodiment of the methods described herein, hematopoietic progenitor cell engraftment is assessed by detecting and/or measuring the level of recovery of neutrophils in an individual.

Efficacy

The efficacy of a given treatment to enhance hematopoietic progenitor cell engraftment can be determined by the skilled clinician. However, a treatment is considered "effective treatment," as the term is used herein, if any one or all of the signs or symptoms of e.g., poor hematopoietic progenitor cell engraftment are altered in a beneficial manner, other clinically accepted symptoms are improved, or even ameliorated, e.g., by at least 10% following treatment with an agent that alters adipocyte metabolism. Efficacy can also be measured by a failure of an individual to worsen as assessed by hospitalization, need for medical interventions (i.e., progression of the disease is halted), or incidence of engraftment failure. Methods of measuring these indicators are known to those of skill in the art and/or are described herein. Treatment includes any treatment of a disease in an individual or an animal (some non-limiting examples include a human, or a mammal) and includes: (1) inhibiting the disease, e.g., preventing engraftment failure; or (2) relieving the disease, e.g., causing regression of symptoms. An effective amount for the treatment of a disease means that amount which, when administered to a mammal in need thereof, is sufficient to result in effective treatment as that term is defined herein, for that disease. Efficacy of an agent can be determined by assessing physical indicators of, for example hematopoietic stem cell engraftment, such as e.g., neutrophil production, white blood cell count, hematopoietic cell numbers, presence/absence of anemia etc. Efficacy can be assessed in animal models of bone marrow transplantation, for example treatment of a rodent following bone marrow transplantation, and any treatment or administration of the compositions or formulations that leads to an increase of at least one symptom of hematopoietic progenitor engraftment.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

Figure 1A:
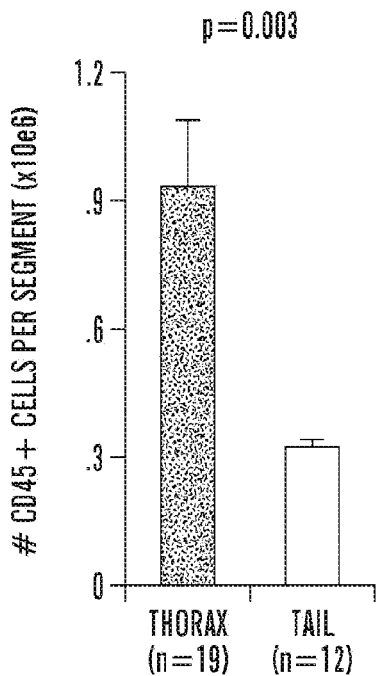
FIGS. 1a-1h: Hematopoietic stem cells and progenitors are reduced in number, frequency and cycling capacity in adipocyte-rich bone marrow during homeostasis.
Figure 1B:
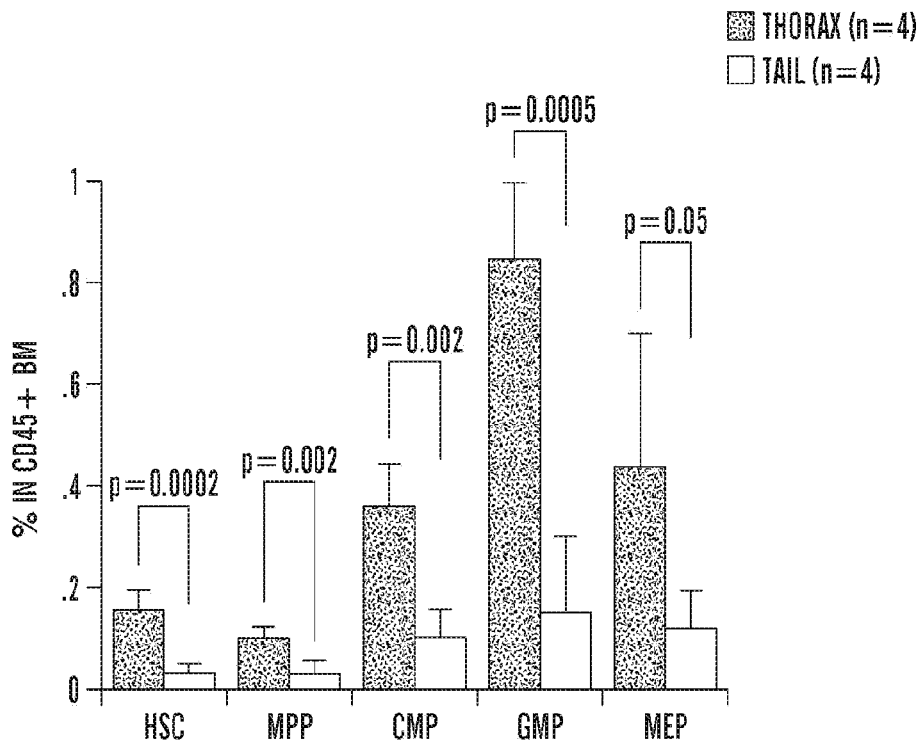

The Adipocytic Compartment Modulates Hematopoiesis and Osteogenesis in the Bone Marrow Studies of bone marrow histology indicate that adipocyte content correlates inversely with hematopoietic content of the marrow. In the study described herein, it was hypothesized that adipocytes play an active role in perpetuating the non-hematopoietic state of fatty bone marrow. To investigate how bone marrow adipocytes influence hematopoiesis during homeostasis, the mouse skeleton was surveyed for adipocyte-rich areas that manifest fatty bone marrow in the absence of underlying pathology. Decalcified thoracic vertebra and fourth tail segments of 12 week old C57BL/6J mice were stained with hematoxylin and eosin (H&E) stain (data not shown), indicating that the spine of adult mice harbours a proximal to distal gradient of bone marrow adipocytes: thoracic vertebrae contain virtually no adipocytes, while vertebrae starting at the level of the third or fourth tail segments are consistently adipocytic. Bone marrow was isolated from the thoracic and tail vertebrae of 12 week-old mice and the hematopoietic stem cell and short-term progenitor compartments were quantified both phenotypically and functionally (schema in FIG. 5). It was found that BM from tail vertebrae contains only 25% as many CD45+ hematopoietic cells per segment as thoracic BM, thus confirming the reduced overall hematopoietic cellularity evident by histology (FIG. 1a). Contiguous frozen sections of tail bone marrow were stained with either Oil Red O to identify adipocytes or H&E staining to identify cell nuclei (data not shown), and indicate that there are less hematopoietic progenitors during homeostasis in adipocyte-rich tail bone marrow. Using flow cytometry, the relative frequency of hematopoietic stem cells (HSC, ckit+Sca1+Lin-Flk2− or KLSF), multipotent progenitors (MPP), common myeloid progenitors (CMP), granulocyte-monocyte progenitors (GMP), and megakaryocyte-erythroid progenitors (MEP) in these different regions of the spine were determined (Christensen J L, et al., *Proc Natl Acad Sci USA*. 98, 14541-6 (2001)). It was found that the percentage of all progenitor classes were reduced 2-3 fold in the CD45+ hematopoietic cells of adipocyte-rich BM of the tail vertebrae compared to non-adipocytic BM from the thoracic vertebrae (FIG. 1b, FIG. 6a).

Figure 1C:
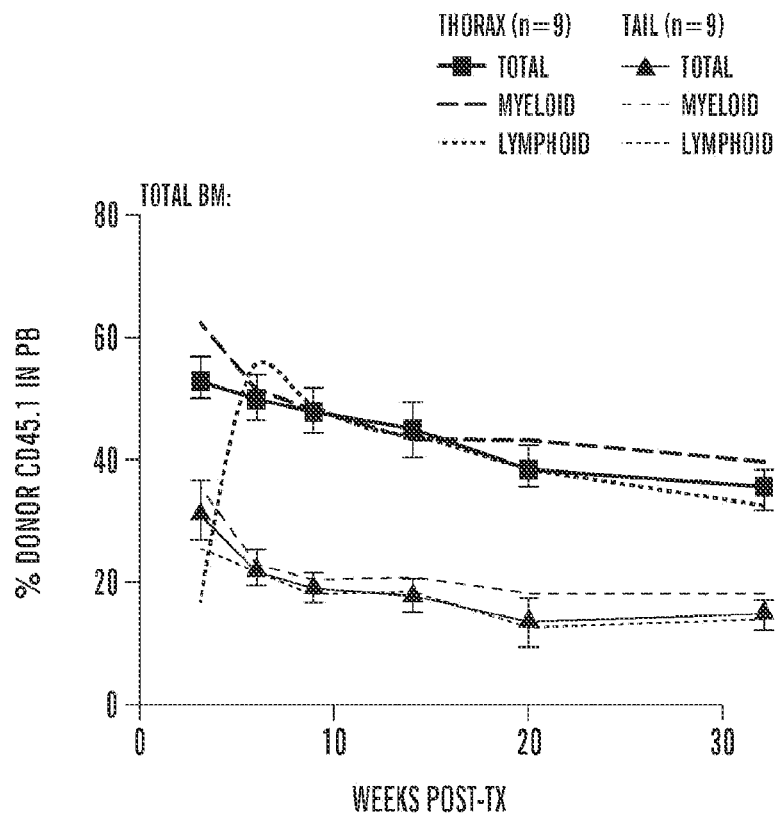
Figure 1D:
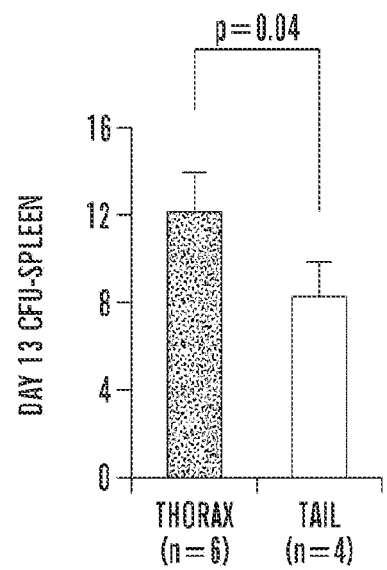
Figure 1E:
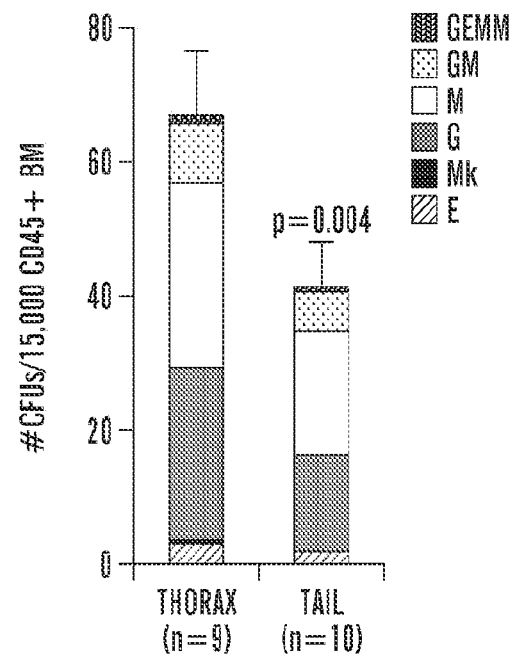

Congruent with the FACS phenotype data, it was observed that long-term repopulating HSCs, short-term repopulating progenitors, spleen colonies and methylcellulose colony forming units were reduced 1.5-3 fold in adipocyte-rich BM from tail vertebrae as compared to adipocyte-free BM from the thoracic vertebrae (FIGS. 1c-1e). This phenomenon does not seem defined by age nor weight-bearing status, for a similar reduction in the frequency of short-term progenitors was observed as determined by FACS and CFU assays in younger (4 week-old) and older mice (13 months), as well as in another consistently fatty yet weight-bearing region of the mouse skeleton, the distal tibia (FIGS. 7a-7e). Bone marrow of wildtype adult mice is consistently fatty as assessed using H&E staining of a distal tibia from a 12-week old wildtype mouse (data not shown). In addition, H&E staining was performed on adipocyte-free tibias of wildtype mice compared to the adipocyte-rich obese, leptin deficient (ob/ob) mice (data not shown), indicating that adipocyte-rich bone marrow from obese mice has less hematopoietic progenitors. Reduced frequency of CMPs and primitive CFUs also accompany the increased BM adiposity of femurs from leptin deficient obese mice (FIG. 8a-8c).

Differentiation of a bone marrow stroma derived OP9 cell line into an adipocytic culture was performed by treatment of the cells with IBMX, dexamethasone, and insulin for 17 days. Oil Red O staining indicated successful differentiation as compared to confluent, undifferentiated cultures (data not shown). KLS (ckit+Lin-Sca1+) cells were FACS sorted and co-cultured with the undifferentiated or adipocytic stroma in the absence of hematopoietic cytokines (data not shown). Results indicate that BM-derived adipocytes are sufficient to reduce the expansion of hematopoietic cells on stromal co-cultures in vitro even in a non-contact transwell layout, demonstrating the presence of diffusible adipocyte-derived inhibitors of hematopoiesis (FIG. 9a-9b). It was concluded that adipocyte-rich marrow is consistently associated with lower absolute levels of hematopoiesis and reduced absolute and relative numbers of progenitors.

Figure 1F:
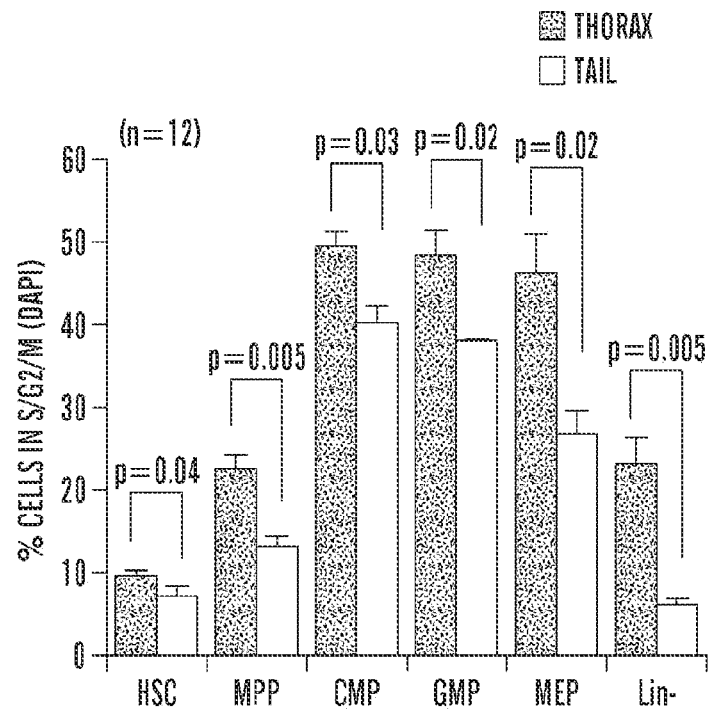
Figure 1G:
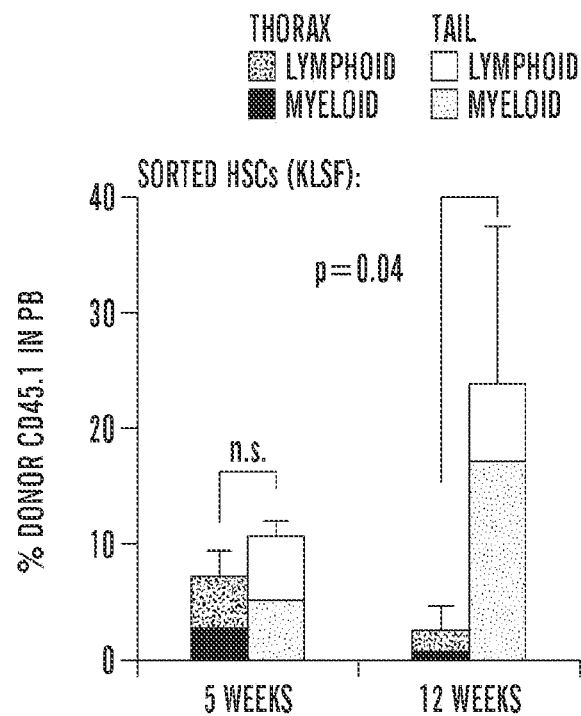
Figure 1H:
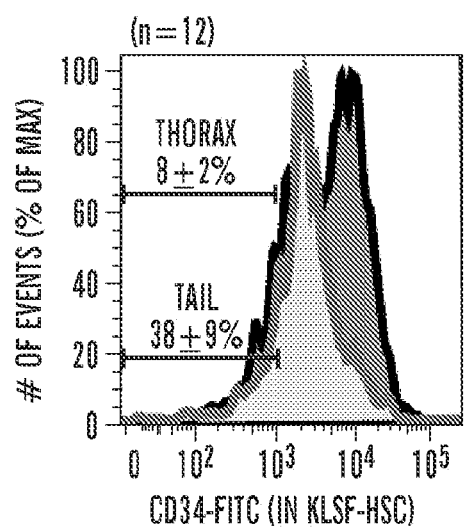

To investigate the mechanism behind the reduced hematopoietic activity of adipocytic BM, cell cycle analysis was performed for each of the progenitor compartments. In all cases, fewer progenitors were found in the replicating phases of the cell cycle (S/G2/M) within the adipocyte-rich BM (FIG. 1f, FIG. 10a). Early progenitors (HSC/MPP) presented no significant difference in their $G_0/G_1$ ratio, while late progenitors (GMP/CMP/MEP) presented a significant increase in the $G_0/G_1$ ratio within the adipocyte-rich tail BM (supplementary FIG. 6b). In order to determine if the slow-cycling HSCs within the tail BM were functional, as opposed to senescent, HSCs were FACS-sorted (ckit+Lin-Sca1+Flk2−, KLSF) and transplanted competitively into lethally irradiated mice. No difference was observed in repopulating activity between HSCs from tail and thorax in the first month post-transplant. However, multilineage long-term engraftment was significantly higher in HSCs purified from tail BM (FIG. 1g), suggesting that the slow-cycling progenitors in adipocytic tail BM are relatively quiescent and not senescent. This is consistent with the relative predominance of CD34low HSCs within the KLSF fraction of tail BM (FIG. 1h), a phenotype associated to long-term repopulation activity (Osawa M, et al., *Science* 273, 242-5 (1996)). Taken together, these data establish tail vertebrae as a model for the study of fatty marrow in the mouse, and demonstrate that adipocyte-rich marrow is consistently accompanied by perturbations of normal hematopoietic homeostasis. HSCs and short-term progenitors are functionally reduced on a per cell basis in fatty marrow due to reduced cycling at the level of the HSC, MPP and CMP compartments.

In order to determine if the association between adipocytic marrow and reduced hematopoietic progenitor frequency is purely correlative, or whether adipocytes actively compromise hematopoiesis in adipocyte-rich BM, the lipoatrophic "fatless" A-ZIP/F1 mouse was studied; the A-ZIP/F1 mouse cannot form adipocytes due to the expression of a dominant negative form of C/EBP under the adipocyte fatty-acid binding protein 4 (aP2/FABP4) promoter (Moitra J, et al. *Genes Dev.* 12, 3168-81 (1998)).

Decalcified H&E stains from 6-week old FVB wild-type mice indicate the presence of fatty marrow, while decalcified H&E stains from 6-week old FBV.A/ZIP-F1 fatless mice indicate the presence of red marrow in the fourth tail segment (data not shown). In contrast to wildtype mice, it was found that the absence of adipocytes in fatless A-ZIP/F1 mice rescued hematopoiesis in the tail, such that A-ZIP/F1 mice presented no significant difference in the frequency of CFUs from thorax or tail BM (FIG. 11a), indicating that compromised osteogenesis due to the non-weight-bearing nature of these bones cannot explain the hematopoietic defect of wild-type, adipocyte-rich tail vertebrae (Pan Z, et al. *Stem Cells Dev.* 17, 795-804 (2008)).

Figure 12A:
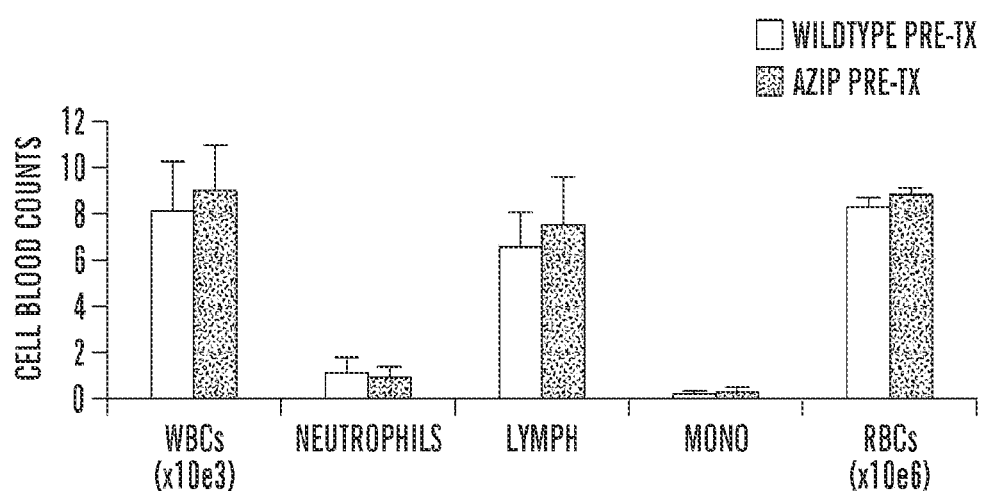
Figure 12B:
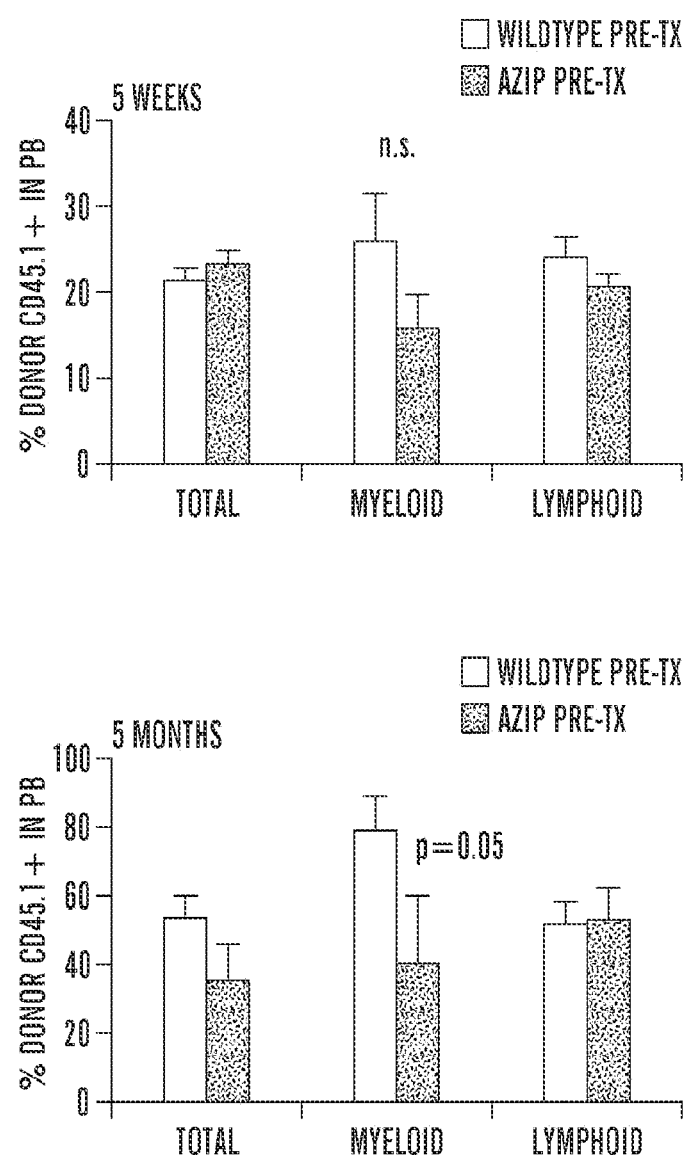

H&E staining was performed on 6-week old FVB wildtype and FVB.A/ZIP/F1 fatless femurs, indicating that there is no difference in the adipocyte-poor bone marrow prior to transplantation in the two groups of mice (data not shown). Importantly, although fatless A-ZIP/F1 mice are diabetic, their blood counts were similar to controls during homeostasis, and their femoral BM showed no competitive advantage over BM from wild-type littermates, arguing that the diabetic milieu does not account for the observed alterations in the hematopoietic compartment (FIGS. 12a-b). It was therefore concluded that the presence of adipocytes is necessary to observe reduced hematopoiesis in adipocyte-rich tail bone marrow.

Figure 2A:
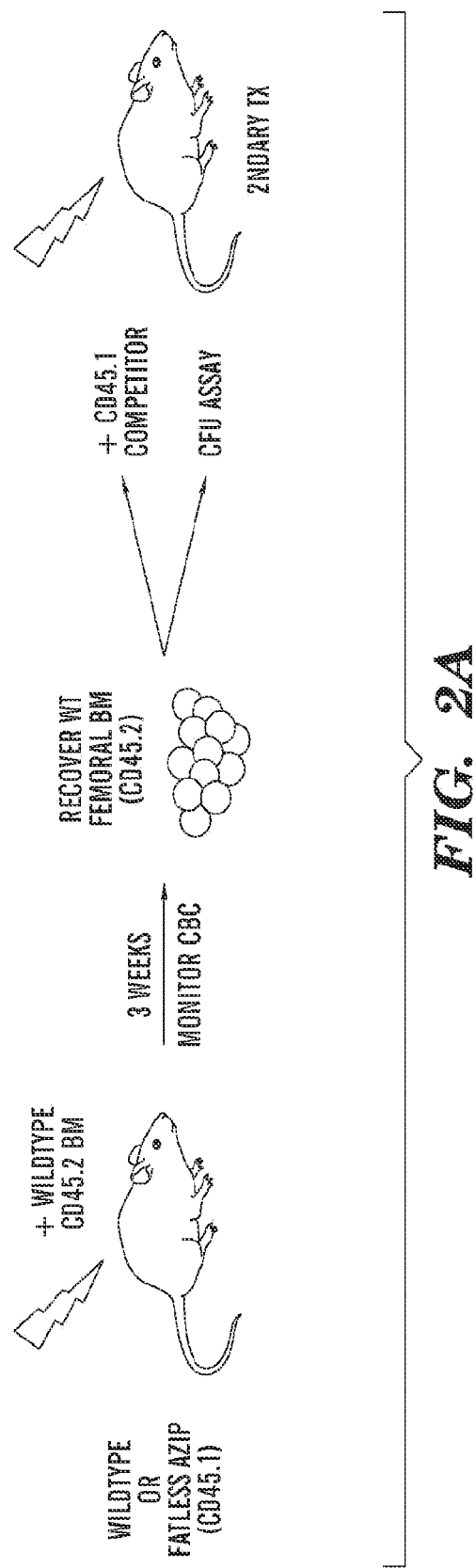
Figure 2B:
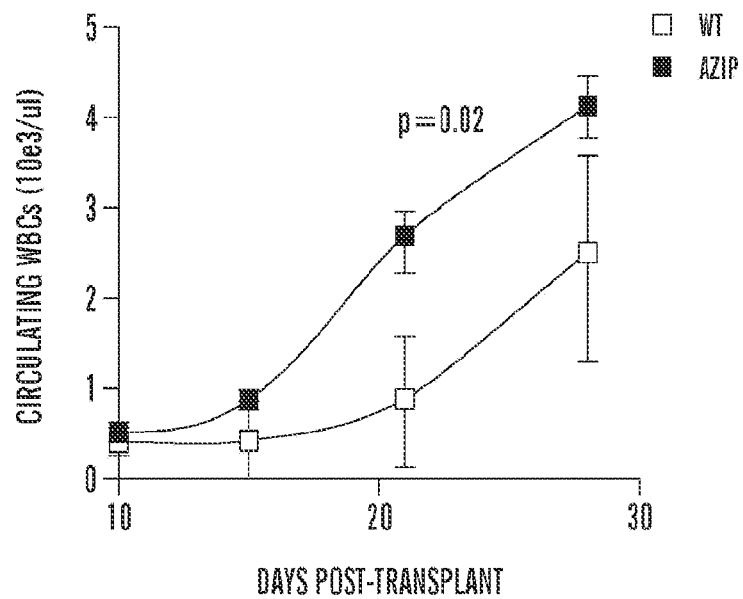
Figure 2C:
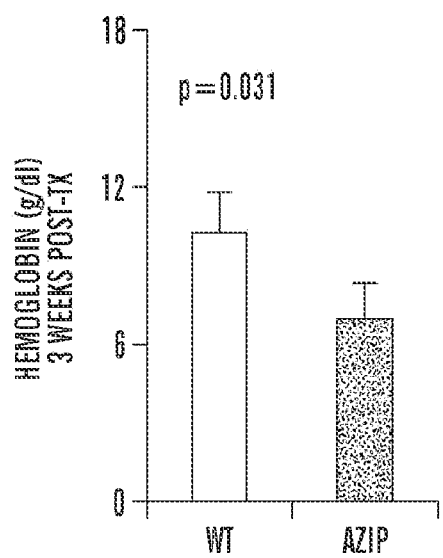
Figure 2D:
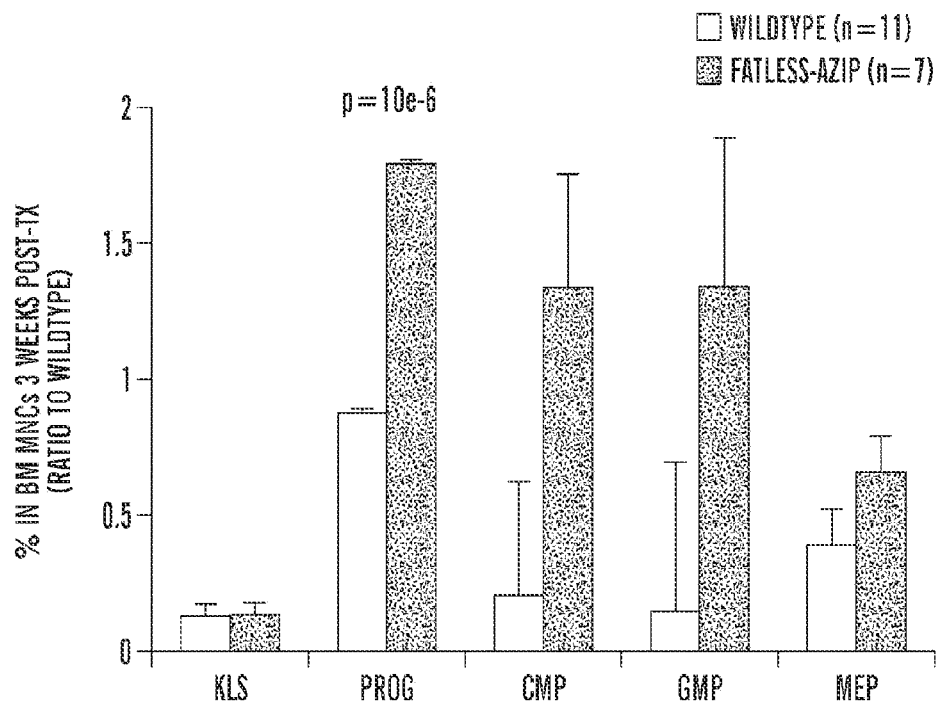
Figure 2E:
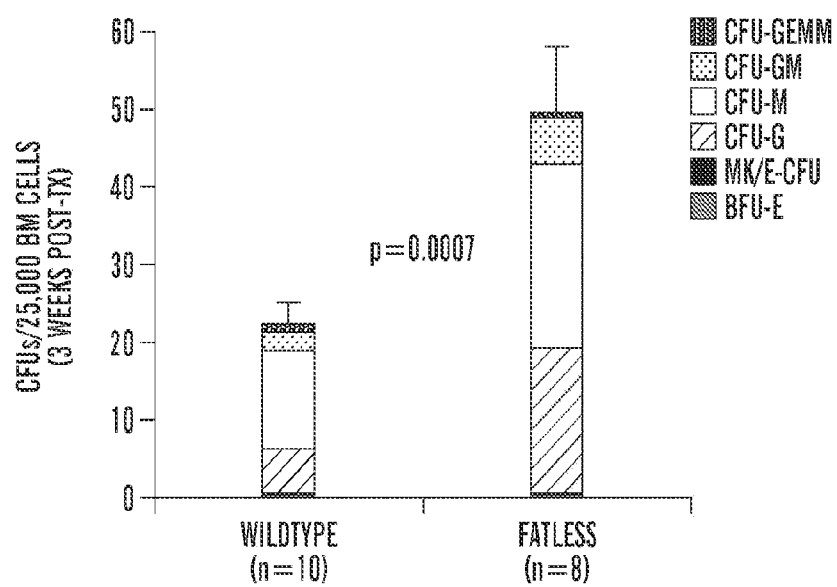
Figure 2F:
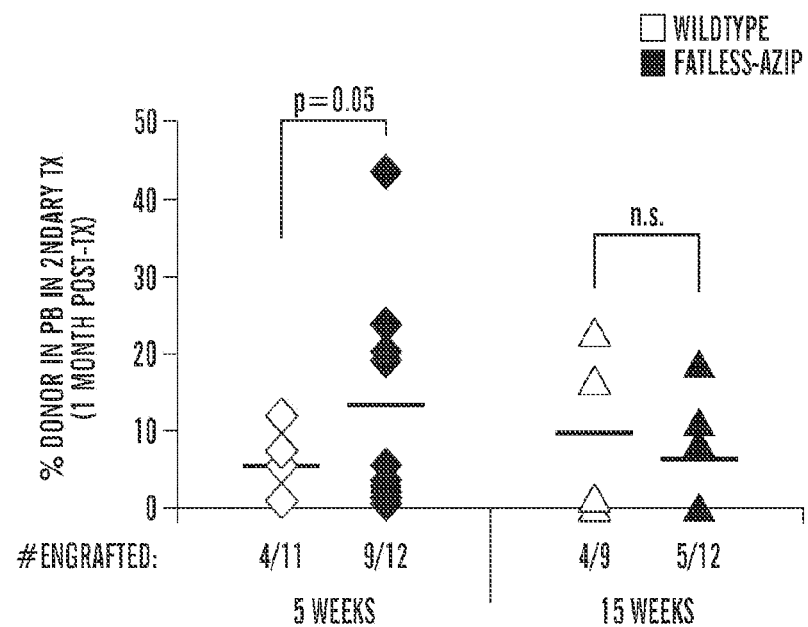
Figure 12C:
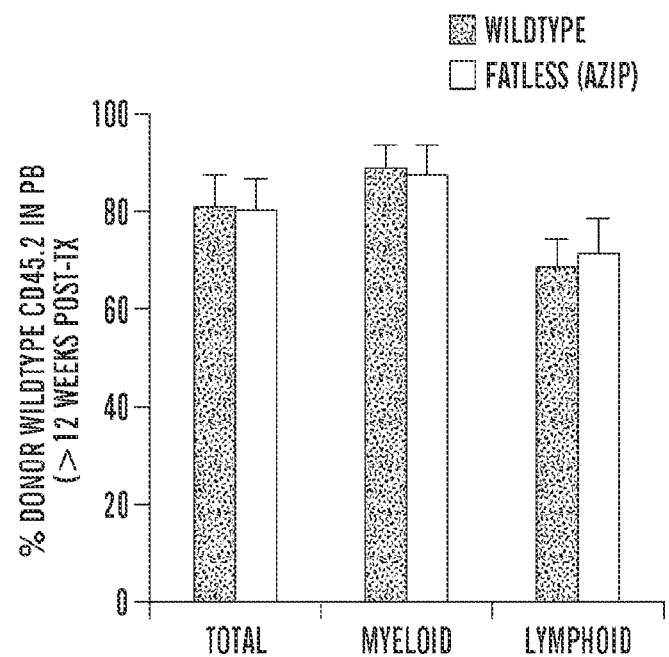
Figure 12D:
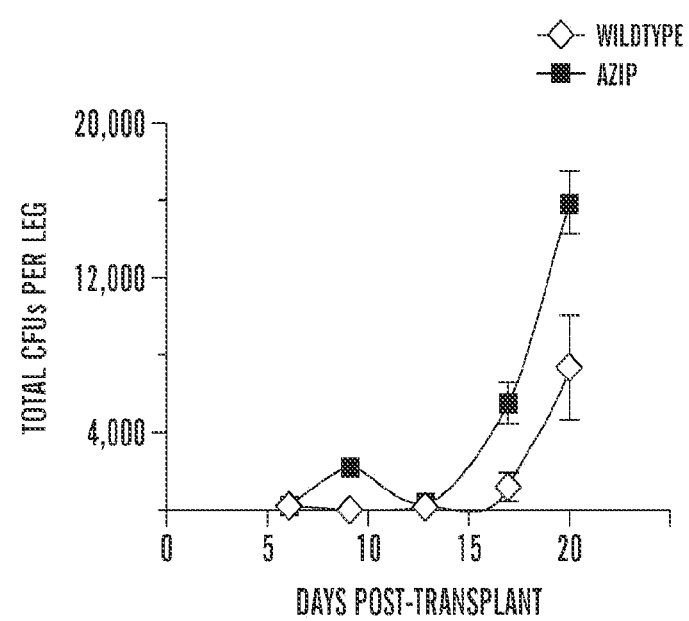

The effect of adipocytes on hematopoietic recovery was analyzed following bone marrow transplantation. Between the second and fourth week after lethal irradiation, the bone marrow space throughout the mouse skeleton becomes fully replaced by adipocytes. During this post-transplant period mice (and human patients) depend on fast cycling, short-term hematopoietic progenitors to rescue their otherwise lethal pancytopenia (Yang L, et al. *Blood* 105, 2717-23 (2005)). It was predicted that a lack of adipocyte formation in the A-ZIP/F1 fatless mouse would enhance hematopoietic recovery in the post-transplant period through increased proliferation of short-term hematopoietic progenitors. Wildtype BM (CD45.2) were transplanted into either wildtype or fatless A-ZIP/F1 littermate recipients (CD45.1, FIG. 2a). In contrast to control mice, A-ZIP/F1 fatless mice exposed to lethal doses of irradiation produced markedly fewer adipocytes in the bone marrow cavity as assessed by femoral hematoxylin and eosin staining in the third week post-transplant (data not shown). Leukocyte recovery was monitored in the post-transplant period and it was found that recovering A-ZIP/F1 fatless mice have up to 4 times higher leukocyte counts in peripheral blood relative to their wild-type controls (FIG. 2b). A significantly accelerated recovery was observed in the hemoglobin content of peripheral blood (FIG. 2c). Importantly, both wild-type and A-ZIP/F1 fatless recipients showed comparable high-level long-term donor chimerism after the primary transplant (FIG. 12c). In the third week post-transplant, the donor CD45.2 BM from the adipocyte-rich wildtype or the adipocyte-free AZIP/F1 femurs were recovered. A pronounced increase in hematopoietic progenitors in the recovering CD45.2 BM isolated from fatless A-ZIP/F1 mice was found as determined by flow cytometry (FIG. 2d), by methylcellulose colony forming assays (FIG. 2e and FIG. 12d) and by short-term competitive repopulation into secondary recipients (FIG. 20. Collectively, these results indicate that the lack of bone marrow adipocytes in A-ZIP/F1 fatless recipient mice enhances hematopoietic recovery of the marrow after lethal irradiation, in particular at the level of short-term progenitors, and further supports the conclusion that the presence of adipocytes in fatty marrow hinders hematopoietic progenitor expansion.

During these studies, it was observed that bone marrow ablation in lethally irradiated A-ZIP/F1 fatless mice was accompanied by marked osteogenesis. High-resolution microCT (computerized tomography) was used to analyze pre/post-transplant tibias from wildtype or fatless A-ZIP/F1 mice 20 days after lethal ablation and indicates that trabecular bone was notably increased in the femurs of transplanted A-ZIP/F1 fatless mice compared to wild-type controls (data not shown). This phenomenon was also apparent in the tail and in mice that were lethally ablated but received no transplant as assessed by hematoxylin and eosin staining (data not shown). The hematoxylin and eosin stain of tail vertebrae from the pre-transplant period to 2-months post-transplant shows the evolution of hematopoiesis and osteogenesis, indicating that a lack of bone marrow adipocytes (as in fatless mice post-irradiation) enhances hematopoietic progenitor expansion also in the tail. High-resolution micro-Computerized Tomography (mCT) confirmed a 5-fold increase in trabecular bone that was specific to fatless A-ZIP/F1 mice after BM transplantation (FIGS. 3a-b). Incorporation of $^{18}$F measured by positron emission tomography (mPET) confirmed increased bone metabolism, indicating new bone deposition in A-ZIP/F1 fatless tails and tibias after bone marrow transplantation that was maximal in the second week post-transplant (FIG. 3c). In addition, H&E staining of femurs from lethally irradiated wildtype or A-ZIP/F1 mice that received no bone marrow transplant when sacrificed at day 12 post-transplant, demonstrated marked osteogenesis in the absence of adipogenic or hematopoietic expansion (data not shown). These data show that simultaneous ablation of both the hematopoietic and the BM adipocyte compartment can induce osteogenesis (Calvi L M, et al. *Nature* 425, 841-6 (2003); Zhang J, et al. *Nature* 425, 836-41 (2003)), which promotes a more supportive environment for hematopoietic reconstitution. This could explain the positive effect of adipocyte ablation in BM engraftment. This observation is compatible with a previous study revealing that surgical removal of the fatty marrow in rabbit tibias induces transient hematopoietic infiltration of the marrow, accompanied by new osteoid and trabecular bone formation (Tavassoli M, et al. *Blood* 43, 33-8 (1974)). Preventing the formation of BM adipocytes without hematopoietic ablation does not cause osteogenesis (Botolin S, and McCabe L R. *J Cell Physiol.* 209, 967-76 (2006)), indicating that osteogenesis can only be induced when both the adipocytic and hematopoietic compartments are simultaneously ablated. Without wishing to be bound by theory, these data indicate a three-way co-regulation within the BM compartment of hematopoiesis, osteogenesis and adipogenesis.

Finally, it was tested whether pharmacologic antagonism of adipogenesis could enhance bone marrow engraftment in wild-type mice. The PPARγ inhibitor Bisphenol-A-DiGlycidyl-Ether (BADGE) has been demonstrated to prevent bone marrow adipocyte formation in vitro and in vivo in models of streptozotocin-induced diabetes (Wright H M, et al. *J Biol Chem.* 275, 1873-7 (2000); Botolin S, and McCabe L R. *J Cell Physiol.* 209, 967-76 (2006)). Importantly, BADGE does not enhance hematopoietic colony formation in vitro, when BM cells are isolated from their stromal microenvironment. BADGE was administered to lethally irradiated mice for the two weeks following bone marrow transplantation, and successful inhibition of BM adipocyte formation was observed by H&E staining of femurs from mice sacrificed on day 17 post-transplant, when the donor CD45.2 wildtype bone marrow was recovered and purified by FACS (data not shown). Higher peripheral blood leukocyte counts (FIG. 4a), and an enrichment in colony forming units (FIG. 4b) was also observed at this time. These results demonstrate that the negative influence of adipocytes on post-transplant hematopoietic engraftment can be overcome pharmacologically, and indicate that PPARγ inhibitors, or other adipocyte inhibitors such as the novel aP2 inhibitor BMS309403 (Furuhashi M, et al. *Nature* 447, 959-65 (2007)), can serve as adjuvants to hematopoietic recovery in the context of bone marrow transplantation.

Collectively, these results contradict the classical dogma that bone marrow adipocytes act exclusively as passive space fillers in the hematopoietic milieu. It is demonstrated herein that adipocyte-rich marrow is associated with a decreased frequency of progenitors and relative stem cell quiescence. Moreover, it was observed that mice genetically deficient in adipogenesis show accelerated hematopoietic recovery after lethal bone marrow ablation, a phenomenon that can be reproduced pharmacologically in wild-type mice through PPARγ inhibition. These results indicate a novel therapeutic approach to enhance hematopoietic engraftment following bone marrow or cord blood transplantation, or to ameliorate aplasia in genetic bone marrow failure syndromes. Without wishing to be bound by theory, these results indicate a mechanism for the recent reports of myelosuppression (Digman C, et al. *Ann Intern Med.* 143, 465-6 (2005); Maaravi Y, and Stessman J. *Diabetes Care* 28, 1536 (2005); Berria R, et al. *Clin Pharmacol Ther.* 82, 275-81 (2007)) in patients treated with the PPARγ agonist rosiglitazone, a popular diabetes drug known to increase marrow adiposity (Lazarenko O P, et al. *Endocrinology* 148, 2669-80 (2007)).

These data indicate a predominantly suppressive influence of adipocytes on hematopoiesis within the bone marrow microenvironment. BM adipocytes have been shown to be less supportive of hematopoiesis in vitro than their undifferentiated stromal or pre-adipocytic counterparts, in part due to reduced production of growth factors such as GM-CSF and G-CSF (Nishikawa M, et al. *Blood* 81:1184-92 (1993); Cone J, et al. *J Cell Physiol.* 208, 282-288 (2006)). Moreover, adipose tissue secretes neuropillin-1 (Belaid-Choucair Z, et al. *Stem Cells* 26, 1556-64 (2008)), lipocalin 2 (Miharada K, et al. *J Cell Physiol.* 215, 526-37 (2008); Yan Q W, et al. *Diabetes* 56, 2533-40 (2007)), adiponectin (Yokota T, et al. *Blood* 96, 1723-32 (2000)) and TNFalpha (Zhang Y, et al. *Blood* 86, 2930-7 (1995); Hotamisligil G S, et al. *Science* 259, 87-91 (1993)), each of which can impair hematopoietic proliferation. Of note, TNFalpha and adiponectin inhibit progenitor activity while positively influencing the most primitive HSCs (Zhang Y, et al. supra; DiMascio L, et al. *J Immunol.* 178, 3511-20 (2007)), a phenomenon compatible with the hypothesis that adipocytes prevent hematopoietic progenitor expansion while preserving the most primitive hematopoietic stem cell pool. Adipocytes and osteoblasts originate from mesenchymal stem cells within the bone marrow, where both compartments hold a reciprocal relationship (Nuttall M E, and Gimble J M. *Curr Opin Pharmacol.* 4, 290-4 (2004)). Balancing the supportive role of the osteoblast in the HSC niche, the data described herein implicate adipocytes as negative regulators of hematopoiesis.

The bone marrow is a complex microenvironment comprising both positive and negative regulators in order to maintain homeostasis and rapid response to cytopenias. Further studies will address the molecular players involved in the hematopoietic inhibition imposed by fatty marrow, which are likely to involve adipocyte-specific mediators as well as the loss of osteoblast and mesenchymal-derived hematopoietic supportive factors.

Osteoblasts and endothelium constitute functional niches that support hematopoietic stem cells (HSC) in mammalian bone marrow (BM) (Calvi L M, et al. supra; Zhang J, et al. supra; Kiel, M. J., et al. *Cell* 121, 1109-1121 (2005)). Adult BM also contains numerous adipocytes, whose numbers correlate inversely with the hematopoietic activity of the marrow during homeostasis and BM aplasia. At birth, hematopoietic red marrow occupies virtually the entirety of the bone marrow space. With age, non-hematopoietic fatty marrow gradually predominates in most non-axial sites in the skeleton of large animals (Neumann E. *Centralblatt für die medicinischen Wissenschaften* 18, 321-323 (1882)). This "fatty degeneration" of the marrow is a dynamic and reversible process illustrated by the fact that disorders of excess hematopoiesis, such as pernicious anemia or leukemia, are typically accompanied by hematopoietic infiltration of the fatty marrow of the long bones (Calvo W, *Blood* 47, 593-601 (1976); Litten M. and Orth J. *Berliner klinische Wochenschrift* 51, 743-751 (1877)). Fatty infiltration of the hematopoietic red marrow follows irradiation or chemotherapy and is a diagnostic feature in biopsies from patients with marrow aplasia (Neumann E. supra).

Herein it is shown that murine hematopoiesis is reduced in adipocyte-rich marrow during homeostasis, and that adipocytes antagonize marrow recovery post-irradiation. By flow cytometry, colony forming assay, and competitive repopulation, a reduced frequency of HSCs and short-term hematopoietic progenitors in the adipocyte-rich vertebrae of the tail was found compared to the adipocyte-free vertebrae of the thorax. In lipoatrophic A-ZIP/F1 "fatless" mice, which are genetically incapable of forming adipocytes (Moitra J, et al. supra), post-irradiation marrow engraftment is accelerated relative to wild type mice and is accompanied by an osteogenic reaction in the ablated BM. Likewise, pharmacologic inhibition of adipocyte formation with the PPARγ inhibitor Bisphenol-A-DiGlycidyl-Ether (BADGE) (Wright H M, et al. supra) enhances hematopoietic recovery after BM transplant. These data implicate adipocytes as predominantly negative regulators of the bone marrow microenvironment, and demonstrate that antagonizing adipogenesis is advantageous for enhancing hematopoietic recovery in the setting of bone marrow transplantation.

Methods

Methods Summary—

Thorax, tibias and tails for homeostasis studies were isolated from wildtype C57BL6/J mice. When BM transplantation was performed, B6.SJL-Ptprca Pep3b/BoyJ were used as donors to take advantage of the CD45.1/CD45.2 allelic system (Jackson Laboratories #0002014). Bone marrow transplantation and CFU-Spleen assays were performed on lethally irradiated mice (two 5.5Gy doses separated by 3 hrs)

and cells were administered by tail vein injection within 24 hrs of lethal irradiation. For competitive transplantation, samples were competed against 250,000 recipient-matched competitor femoral bone marrow. FVB wildtype litter-mates mice were used as controls for FVB.A-ZIP/F1 fatless mice. During BM transplantation assays FVB or FVB.A-ZIP/F1 mice (CD45.1) received 200,000 MHC-matched ($H^q$) wild-type BM from DBA/1J mice (CD45.2). Secondary transplants were performed through recovery of the CD45.2 DBA/2 BM passed through the FVB wildtype or FVB.A-ZIP/F1 microenvironment, which was then transplanted into FVB (CD45.1) recipients together with 250,000 FVB (CD45.1) wildtype competitor BM cells. For pharmacological inhibition of adipocyte formation, BM transplants were performed in wild-type female FVB mice as described above, except that 30 mg/kg BADGE or control vehicle (DMSO 10%) were administered in daily intraperitoneal injections starting one day prior to irradiation and continuing until day 14 post-transplant. Solutions were made such that 500 mg BADGE (Fluka) was resuspended in 8.3 ml DMSO (Sigma) and diluted in PBS to a final concentration of 10% DMSO for administration at 30 mg/kg in 100 ul. Aliquots were stored at $-20°$ C. and thawed daily. Multicolor flow cytometry was performed in a special order BD five-laser LSRII flow cytometer. Cell cycle analysis was performed with DAPI (Sigma) in cells fixed in 2% paraformaldehyde for 15 min at 4° C. For all statistical analysis an un-paired two-tailed Student's t-test was performed assuming experimental samples of equal variance. Error bars and confidence intervals represent the standard error of the mean (SEM) unless otherwise indicated.

Animals—

All mice were sex, weight and age-matched and were purchased from Jackson Laboratories, then breeding colonies were established in house. Experiments were carried out with Institutional Animal Care and Use Committee approval from Children's Hospital, Boston.

Bone Marrow Preparation—

Femurs, thorax and tails were isolated free of skeletal muscle and tendons; when appropriate, the spinal cord was carefully removed. Bones were crushed independently in IMDM with mortar and pestle, filtered through a 70 μm filter and washed with PBS. A sample was removed, stained with CD45-FITC (1:200) and 7-AAD (1:100) in 50 ul and the volume raised to 500 ul with PBS and reference beads (Sigma). A viable CD45+ cell count was then obtained with a F500-Coulter flow cytometer. Red blood cells from bone marrow in homeostatic conditions (pre-transplant) were lysed with RBC lysis buffer (Sigma). Bone marrow from early post-transplant was not lysed and efforts were made to perform minimal manipulation before CFU plating or secondary transplantation; in this case, RBCs were not accounted for, though, because cell counts were done based on CD45+ counts.

Flow Cytometry—

Multicolor analysis for progenitor and stem cell quantification was optimized for a FACS-Aria Instrument with an additional UV laser. Cells were stained in PBS 2% FCS for 1 hour with CD34-FITC (1:50, BD), Flk2-PE (1:100, BD), Lineage cocktail-PECyS (Ter119, B220, CD19, CD3, CD4, CD8, Nk1.1 from eBiosciences; mix 1:1 except CD3 2:1, and use 1:200), FcγRIII/II-PECy7 (1:200, Biolegend), ckit-APC (1:200, BD), CD45.1 or CD45.2-APCCy7 (1:100, Biolegend), CD45-biotin (1:200, BD), Streptavidin-Pacific Orange (1:2000, Invitrogen), and Sca1-Pacific Blue (1:100 Biolegend). For cell cycle analysis, bone marrow cells were stained in cold 2% IFS as above and fixed in cold 2% PFA for 15 minutes, then washed, stained in DAPI solution for 10 minutes at room temperature (0.1% (v/v) Triton X-100 and 1 μg/ml DAPI in PBS (Wilson A, et al. *Genes Dev* 18, 2747-63 (2004); Pozarowski, P. and Darzynkiewicz, Z. *Methods Mol Biol* 281, 301-311 (2004)), washed and analyzed in a BD five laser LSRII flow cytometer. Ki-67 analysis was done as described by Wilson et al. (Wilson A, et al *Genes Dev* 18, 2747-63 (2004)). Bone marrow cells were stained by cell surface markers (Sca1-FITC (1:100, BD), Lineage-cocktail (1:200), FcγRIII/II-PECy7 (1:200, Abcam), ckit-APC (1:200), CD45-APCCy7 (1:100, BD), CD150-biotin (1:300, BioLegend), Streptavidin-Alexa Fluor 680 (1:200, Invitrogen)), washed, fixed in cold Cytofix/Cytoperm buffer (BD) for 20 minutes, then washed and incubated in Permwash buffer (BD) with Ki-67-PE (1:100, BD) for 5 hours at 4° C. Cells were treated with 1 μg/ml DAPI for 10 minutes, washed and resuspended in PBS 2% FCS immediately prior to acquisition on a BD LSRII flow cytometer.

Progenitor Assays—

Colony forming unit (CFU) assays were performed in complete M3434 methylcellulose (Stem Cell Technologies) following the manufacturer's instructions. Colonies were scored on day 8-10 on coded plates for unbiased counts.

Bone Marrow Transplantation—

Mice were lethally irradiated with 11-12Gy on a split dose separated by 2.5 h and BM transplants were performed within 24 h by tail-vein injection. Engraftment was measured monthly through eye bleed and FACS analysis with CD45.1-FITC (eBiosciences), CD45.2-PE or CD45.2-biotin, CD3-PE, CD19-PE, Mac-1-PE. Gr1-PE, F4/80-APC. All antibodies were ordered from Beckton-Dickinson unless otherwise specified. Mice whose engraftment was below 0.5% were considered non-engrafted and were not taken into account for the calculation of competitive repopulation units.

Stromal Cell Culture and Differentiation—

OP9 cells (ATCC) were expanded in MEMalpha 15% IFS+ pen/strep/glutamine (Gibco) with media changes performed every 3-4 days. Adipocytic differentiation was performed by addition of isobutylmethylxantine (IBMX, Sigma 1000× stock in DMSO) 0.5 mM, insulin 5 ug/ml (Sigma, 1000× stock in PBS) and dexamethasone $10^{-6}$M (Sigma, 1000× stock in ethanol) on the first week to then pass to a maintenance media containing insulin and dexamethasone only for up to 17 days of total differentiation. Differentiation media was changed every 3-4 days. All media changes were made with fresh aliquots, which were kept in the dark at $-20°$ C. Hematopoietic co-cultures with ckit+Lin-Sca1+(KLS) hematopoietic stem cells were performed in IMDM 10% IFS at 37° C. and 5% CO2; media was changed on the seventh day of co-culture. For co-cultures, 2000 FACS sorted KLS were plated per well. Transwell assays used 12 mm polyester inserts with 0.4 μm pore size (Corning) with adipocytic or undifferentiated OP9 cells plated in the bottom of the plate while undifferentiated OP9s were co-cultured with KLS in the upper insert.

MicroPET Analysis—

For micro Positron Emission Tomography (mPET), mice were administered equal doses (5.6-9.3 MBq) of sodium fluoride-18 (F-18) by tail-vein injection. Animals were imaged prior to bone marrow transplantation, and the same cohort of animals was re-assayed at different times post-transplant. Exactly 30 min after the F-18 injection, mice were imaged with a Focus 120 microPET scanner (Siemens). For normalization, the total dose injected was determined immediately pre- and post-imaging by introducing the anesthetized mouse in the dose calibrator and calculating the mid-acquisition dose as the average of the pre- and post-acquisition measurements adjusted by time decay. ASIPro software (Siemens)

was then used for image analysis. To determine the F-18 uptake in tibias and tails, a 3D ROI (region of interest) was created in transverse sections through the selection of six 9×9 pixel planes moving distally from the tibial plate or 12 planes moving distally from the beginning of the free tail. The mean dose in the ROI (Bq/ml) was then normalized to the total injected dose and the ratios from pre to post-transplant F18-uptake were then calculated. When the whole cohort of mice could not be assayed on the same day post-transplant, data from the two closest dates was interpolated.

MicroCT Analysis—

For high-resolution micro Computerized Tomography (mCT) analysis, tibias were dissected, fixed in 10% formalin, and imaged with the Siemens microCAT II system using a 22.75 micrometer pixel size. Beam angle of increment was 1 degree and tube voltage and current were 80 kvp and 450 µA per view as described by Botolin and McCabe L R. *J Cell Physiol.* 209, 967-76 (2006). Each run included wildtype and fatless bones and a calibration phantom to calibrate grayscale values with respect to mass density and maintain consistency. A fixed density threshold was established through normalization to the phantom to separate trabecular bone from bone marrow (1350 mg/ml). Trabecular bone analyses were done with ImageJ and AMIRA image analysis software in a 0.2 mm thick 3D square region of trabecular bone defined at 1 mm under the growth plate of the proximal tibia extending 0.9 mm toward the diaphysis and excluding the outer cortical shell.

All references cited throughout this specification are herein incorporated by reference in their entirety.

The invention claimed is:

1. A method for enhancing hematopoietic progenitor cell engraftment in an individual following hematopoietic progenitor cell transplantation, the method comprising administering to said individual an agent that alters adipocyte metabolism, thereby enhancing hematopoietic progenitor cell engraftment.

2. The method of claim 1, wherein said hematopoietic progenitor cells are derived from bone marrow.

3. The method of claim 1, wherein said hematopoietic progenitor cells are derived from cord blood.

4. The method of claim 1, wherein said agent is selected from the group consisting of a PPAR gamma inhibitor, an ap2/FABP4 inhibitor, and an 11 beta-hydrosteroid dehydrogenase inhibitor.

5. The method of claim 4, wherein said PPAR gamma inhibitor is selected from the group consisting of: bisphenol-A-diglycidyl-ether (BADGE), pioglitazone, 2-chloro-5-nitro-N-4-pyridinyl-benzamide (T0070907), 2-chloro-5-nitrobenzanilide (GW9662), (4-chlorophenyl)-(diemethoxyphosphinyl)-methyl-phosphoric acid-dimethyl ester (mifobate; SR-202), 2-((5,5,8,8-tetramethyl-5,6,7,8-tetrahydro-2-naphthyl)carbonyl)benzoic acid (LG 100641), propanamide, 2,2-dimethyl-N-[5-nitro-3-(2-propen-1-yl)-2 (3H)-thiazolylidene] (PD068235); diclofenac; MK886; (2-thiophenecarboxylic acid, 3-[[[2-methoxy-4-(phenylamino)phenyl]amino]sulfonyl]-methyl ester (GSK0660); benzoic acid, 2-[(5,6,7,8-tetrahydro-5,5,8,8-tetramethyl-2-naphthalenyl)carbonyl]-) (LG100641); benzoic acid, 4-(7,8,9,10-tetrahydro-5,7,7,10,10-[entamethyl-2-nitro-5H-benzo[b]naphtho[2,3-e][1,4]diazepin-12-yl)-) (HX531); and ((4-2((2S,5S)-5-2(-(bis(phenylmethyl)amino)-2-oxoethyl)-2-heptyl-4-oxo-3-thiazolidinyl)butyl)-benzoic acid) (GWO072).

6. The method of claim 4, wherein said ap2/FABP4 inhibitor is selected from the group consisting of BMS309403, N-benzyl-hexahydrocyclohepta[b]indole, and 1,3-oxazinan-2-one and derivatives thereof.

7. The method of claim 4, wherein said 11 beta-hydrosteroid dehydrogenase inhibitor is selected from the group consisting of PF877423, BVT.2733, 4-thiazoleacetamide, 2-[[(3-chloro-2-methylphenyl)sulfonyl]amino]-N,N-diethyl-2-[2-[[3-Chloro-2-methylphenyl_sulfonyl]amino]-1,3-thiazol-4-yl]-N,N-diethylacetamide (BVT.14225), and trifluoromethyl thiazolone.

8. The method of claim 1, wherein the rate of engraftment is enhanced.

9. The method of claim 1, wherein said engraftment is increased within 2-6 weeks following hematopoietic progenitor cell transplantation.

10. The method of claim 1, wherein the agent is administered before, during, or after hematopoietic progenitor cell transplantation.

11. A method for increasing hematopoietic progenitor cell proliferation in an individual following bone marrow transplantation, the method comprising administering to said individual an agent that alters adipocyte metabolism, wherein said agent increases hematopoietic progenitor cell proliferation.

12. The method of claim 11, wherein the individual has had a bone marrow transplant.

13. The method of claim 11, wherein the individual has bone marrow aplasia.

14. The method of claim 11, wherein said agent is selected from the group consisting of a PPAR gamma inhibitor, an ap2/FABP4 inhibitor, and an 11 beta-hydrosteroid dehydrogenase inhibitor.

15. The method of claim 14, wherein said PPAR gamma inhibitor is selected from the group consisting of: bisphenol-A-diglycidyl-ether (BADGE), pioglitazone, 2-chloro-5-nitro-N-4-pyridinyl-benzamide (T0070907), 2-chloro-5-nitrobenzanilide(GW9662), (4-chlorophenyl)-(diemethoxyphosphinyl)-methyl-phosphoric aciddimethyl ester (mifobate; SR-202), 2-((5,5,8,8-tetramethyl-5,6,7,8-tetrahydro-2-naphthyl)carbonyl)benzoic acid (LG 100641), propanamide, 2,2-dimethyl-N-[5-nitro-3-(2-propen-1-yl)-2 (3H)-thiazolylidene] (PD068235); diclofenac; MK886; (2-thiophenecarboxylic acid, 3-[[[2-methoxy-4-(phenylamino)phenyl]amino]sulfonyl]-methyl ester (GSK0660); benzoic acid, 2-[(5,6,7,8-tetrahydro-5,5,8,8-tetramethyl-2-naphthalenyl)carbonyl]-) (LG100641); benzoic acid, 4-(7,8,9,10-tetrahydro-5,7,7,10,10-[entamethyl-2-nitro-5H-benzo[b]naphtho[2,3-e][1,4]diazepin-12-yl)-) (HX531); and ((4-2((2S,5S)-5-2(-(bis(phenylmethyl)amino)-2-oxoethyl)-2-heptyl-4-oxo-3-thiazolidinyl)butyl)-benzoic acid) (GWO072).

16. The method of claim 14, wherein said ap2/FABP4 inhibitor is selected from the group consisting of BMS309403, N-benzyl-hexahydrocyclohepta[b]indole, and 1,3-oxazinan-2-one and derivatives thereof.

17. The method of claim 14, wherein said 11 beta-hydrosteroid dehydrogenase inhibitor is selected from the group consisting of PF877423, BVT.2733, 4-thiazoleacetamide, 2-[[(3-chloro-2-methylphenyl)sulfonyl]amino]-N,N-diethyl-2-[2-[[3-Chloro-2-methylphenyl_sulfonyl]amino]-1,3-thiazol-4-yl]-N,N-diethylacetamide (BVT.14225), and trifluoromethyl thiazolone.

18. The method of claim 11, wherein the agent is administered before, during, or after hematopoietic progenitor cell transplantation.

* * * * *

UNITED STATES PATENT AND TRADEMARK OFFICE
CERTIFICATE OF CORRECTION

PATENT NO. : 8,546,382 B2  
APPLICATION NO. : 13/264423  
DATED : October 1, 2013  
INVENTOR(S) : Olaia M. Naveiras et al.

Page 1 of 1

It is certified that error appears in the above-identified patent and that said Letters Patent is hereby corrected as shown below:

In the Specification:

At column 1, line 14, delete "entirety".

In the Claims:

At column 23, claim 5, line 67, delete "(GWO072)" and insert --(GW0072)--.

At column 24, claim 15, line 52, delete "(GWO072)" and insert --(GW0072)--.

Signed and Sealed this
Seventeenth Day of December, 2013

Margaret A. Focarino
*Commissioner for Patents of the United States Patent and Trademark Office*